(12) United States Patent
Fujii et al.

(10) Patent No.: US 8,205,988 B2
(45) Date of Patent: Jun. 26, 2012

(54) STEREOMICROSCOPE

(75) Inventors: Kouta Fujii, Tokyo (JP); Takefumi Hayashi, Tokyo (JP); Nobuaki Kitajima, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 119 days.

(21) Appl. No.: 12/736,029

(22) PCT Filed: Feb. 18, 2009

(86) PCT No.: PCT/JP2009/000648
§ 371 (c)(1),
(2), (4) Date: Sep. 2, 2010

(87) PCT Pub. No.: WO2009/110175
PCT Pub. Date: Sep. 11, 2009

(65) Prior Publication Data
US 2010/0328608 A1   Dec. 30, 2010

(30) Foreign Application Priority Data
Mar. 3, 2008   (JP) .................. 2008-051809

(51) Int. Cl.
*A61B 3/10* (2006.01)
*G02B 21/00* (2006.01)
*G02B 21/06* (2006.01)

(52) U.S. Cl. ........ 351/205; 351/214; 351/221; 359/368; 359/385

(58) Field of Classification Search .......... 351/200–246; 359/381, 383, 385, 389, 368, 390
See application file for complete search history.

(56) References Cited

U.S. PATENT DOCUMENTS

| 5,619,372 | A | * | 4/1997 | Hellmuth et al. ............. 359/389 |
| 6,705,728 | B2 | * | 3/2004 | Okamoto et al. ............. 351/221 |
| 7,232,222 | B2 | * | 6/2007 | Kogawa et al. ............... 351/221 |
| 2004/0004694 | A1 | | 1/2004 | Sugino et al. |

FOREIGN PATENT DOCUMENTS

| JP | 09-276227 A | 10/1997 |
| JP | 2001-198088 A | 7/2001 |
| JP | 2003-024366 A | 1/2003 |
| JP | 2003-310556 A | 11/2003 |
| JP | 2005-230558 A | 9/2005 |

OTHER PUBLICATIONS

International Search Report dated Mar. 24, 2009 issued in International Application No. PCT/JP2009/000648.

* cited by examiner

*Primary Examiner* — Mohammed Hasan
(74) *Attorney, Agent, or Firm* — Edwards Wildman Palmer LLP

(57) ABSTRACT

In intraocular observation of the eye, the slit lamp microscope 1 causes the illumination light emitted by the illumination system 8 to enter the inside of the eye via the head lens 20 and causes an intraocularly reflected light of this illumination light to enter the observation system 6 via the head lens 20 in a state that an illumination optical axis O2 and an observation axis O1 are arranged so as to be nonparallel and a head lens optical axis OF and the observation optical axis O1 are arranged so as to be separate right and left.

20 Claims, 12 Drawing Sheets

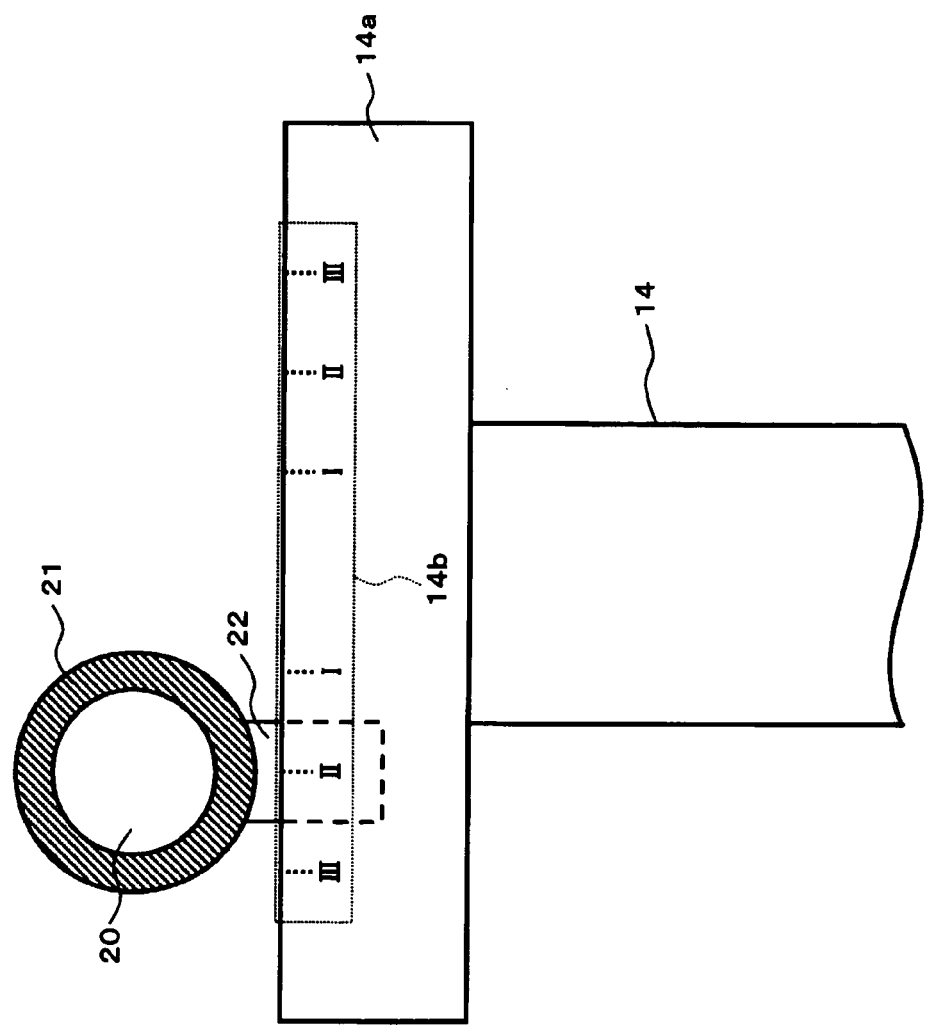

STEREOMICROSCOPE

TECHNICAL FIELD

The present invention relates to a stereomicroscope used in the ophthalmologic field, more specifically, a technique for intraocular observation.

BACKGROUND ART

In the ophthalmologic field, various kinds of stereomicroscopes such as a slit lamp microscope and a surgical microscope are used. An ophthalmologic stereomicroscope is generally configured to enable binocular observation of an eye. Moreover, such a stereomicroscope is configured to enable observation of not only an anterior segment (the cornea and so on) but also the inside of an eye. The "inside of an eye" refers to a site within the pupil, for example, the fundus oculi (the retina) and the vitreous body.

In intraocular observation using a stereomicroscope, a specific lens is placed between an objective lens and an eye. For example, in a slit lamp microscope described in Patent Document 1, a head lens placed in non-contact with an eye is used. Although the head lens is held by a lens holder in Patent Document 1, the head lens may be grasped by the operator and used.

A surgical microscope described in Patent Document 2 is configured to enable intraocular observation in a state that a head lens is placed in non-contact with an eye. Moreover, Patent Document 3 discloses a contact lens placed in contact with an eye during surgery.

In this description, a lens placed between an objective lens and an eye for intraocular observation as described above will be generically referred to as a head lens.
[PATENT DOCUMENT 1]
Japanese Unexamined Patent Application Publication No. 9-276227
[PATENT DOCUMENT 2]
Japanese Unexamined Patent Application Publication No. 2005-230558
[PATENT DOCUMENT 3]
Japanese Unexamined Patent Application Publication No. 2003-24366

DISCLOSURE OF THE INVENTION

Problem that the Invention is to Solve

Conventionally, in intraocular observation using a stereomicroscope, there has been a need to regulate the position of a head lens so that flare resulting from reflection on the surface and rear surface of the head lens does not interrupt an observation field (that is to say, so that a light reflected by the head lens does not enter an observation system). This operation has been performed by trial and error, depending on the technique of the operator. Therefore, it has not been easy to place the head lens in a favorable position.

Further, in intraocular observation using a conventional stereomicroscope, an observation field has been set narrow in order to decrease or eliminate flare caused by the head lens. Therefore, only a narrow range of the fundus oculi has been observed at one time with the conventional stereomicroscope. For example, in intraocular observation using a slit lamp microscope, a slit light has been used as an illumination light, and it has been possible to obtain only a narrow slit-like illumination field. Besides, since setting an observation field has been performed depending on the technique of the operator, it has not been easy to set a favorable observation field.

The present invention has been made in order to solve the aforementioned problems, and an object of the present invention is to provide a stereomicroscope configured to enable intraocular observation with a wide observation field while preventing occurrence of flare.

Means for Solving the Problem

In order to achieve the aforementioned object, in a first aspect of the present invention, a stereomicroscope comprises: an illumination system including a light source configured to output an illumination light and an illumination diaphragm configured to interrupt part of the illumination light, the illumination system being configured to project the illumination light propagated through the illumination diaphragm to an eye; an observation system having an objective lens, and right and left optical systems each configured to guide a light reflected by the eye of the illumination light propagated through the objective lens; a first mechanism configured to move the illumination system in a lateral direction; and a head lens placed between the objective lens and the eye, wherein at the time of intraocular observation of the eye, in a state that an optical axis of the illumination system and an optical axis of the observation system are arranged so as to be nonparallel by the first mechanism and an optical axis of the head lens and an optical axis of the objective lens are arranged so as to be separate in the lateral direction, the illumination light emitted from the illumination system is caused to enter the eye via the head lens, and an intraocularly reflected light of the illumination light is caused to enter the observation system via the head lens.

Further, in a second aspect of the present invention, the stereomicroscope according to the first aspect further comprises a second mechanism configured to support the head lens and move the head lens at least in the lateral direction. In the stereomicroscope, at the time of intraocular observation of the eye, the optical axis of the head lens and the optical axis of the objective lens are arranged so as to be separate in the lateral direction by the second mechanism.

Further, in a third aspect of the present invention, in the stereomicroscope according to the first aspect, at the time of intraocular observation of the eye, in a state that the illumination system is arranged on one of a right side and a left side of the observation system by the first mechanism and the optical axis of the head lens is arranged on the one side of the optical axis of the objective lens, the intraocularly reflected light is caused to enter the optical system on the one side of the right and left optical systems.

Further, in a fourth aspect of the present invention, in the stereomicroscope according to the third aspect, the observation system includes an interrupting part configured to interrupt the light having entered the optical system on the other side of the right and left optical systems.

Further, in a fifth aspect of the present invention, in the stereomicroscope according to the third aspect, the observation system includes a projector configured to project a fixation target to the eye via the optical system on the one side.

Further, in a sixth aspect of the present invention, in the stereomicroscope according to the first aspect, the first mechanism includes a rotation mechanism configured to support the illumination system so as to be rotatable around an axis orthogonal to the optical axis of the illumination system.

Further, in a seventh aspect of the present invention, in the stereomicroscope according to the first aspect, the first mechanism includes a first actuator configured to generate a driving force, the first mechanism being configured to move the illumination system by the generated driving force.

Further, in an eighth aspect of the present invention, the stereomicroscope according to the seventh aspect further comprises: a manipulation part; and a controller configured to, in response to manipulation of the manipulation part, control the first actuator to move the illumination system so that the optical axis of the illumination system and the optical axis of the observation system form a predetermined angle.

Further, in a ninth aspect of the present invention, in the stereomicroscope according to the second aspect, the second mechanism is configured to move the head lens in an anteroposterior direction and/or a vertical direction.

Further, in a tenth aspect of the present invention, in the stereomicroscope according to the ninth aspect, the second mechanism includes a manipulation part used for moving the head lens.

Further, in an eleventh aspect of the present invention, in the stereomicroscope according to the ninth aspect, the second mechanism includes a second actuator configured to generate a driving force, the second mechanism being configured to move the head lens by the generated driving force.

Further, in a twelfth aspect of the present invention, the stereomicroscope according to the eleventh aspect further comprises: a manipulation part; and a controller configured to, in response to manipulation of the manipulation part, control the second actuator to move the head lens so that the optical axis of the head lens and the optical axis of the objective lens are separated at a predetermined distance.

Further, in a thirteenth aspect of the present invention, in the stereomicroscope according to the second aspect: the illumination system further includes a slitting part configured to form a slit for generating a slit light based on the illumination light outputted from the light source, the illumination system being configured to project the slit light to the eye; the first mechanism includes a first actuator configured to generate a driving force, the first mechanism being configured to move the illumination system by the generated driving force; and the second mechanism includes a second actuator configured to generate a driving force, the second mechanism being configured to move the head lens by the generated driving force. The stereomicroscope further comprises: a manipulation part configured to switch from an anterior segment observation mode using the slit light to an intraocular observation mode; and a controller configured to, in response to manipulation of the manipulation part, control the slitting part to end formation of the slit, control the illumination diaphragm to set to a predetermined aperture value, control the first actuator to move the illumination system so that the optical axis of the illumination system and the optical axis of the observation system form a predetermined angle, and control the second actuator to move the head lens so that the optical axis of the head lens and the optical axis of the objective lens are separated at a predetermined distance.

Further, in a fourteenth aspect of the present invention, in the stereomicroscope according to the second aspect, the illumination system further includes a slitting part configured to generate a slit light based on the illumination light outputted from the light source, the illumination system being configured to project the slit light to the eye; the first mechanism includes a first actuator configured to generate a driving force, the first mechanism being configured to move the illumination system by the generated driving force; and the second mechanism includes a second actuator configured to generate a driving force, the second mechanism being configured to move the head lens by the generated driving force. The stereomicroscope further comprises: a manipulation part configured to switch from an intraocular observation mode to an anterior segment observation mode using the slit light; and a controller configured to, in response to manipulation of the manipulation part, control the illumination diaphragm to set to an open aperture value, and control the slitting part to form the slit.

Further, in a fifteenth aspect of the present invention, the stereomicroscope according to the first aspect further comprises: a storage configured to previously store angle relation information that relates a power of the head lens and an angle of the optical axis of the illumination system with respect to the optical axis of the observation system; and a controller configured to receive power information of the head lens placed between the objective lens and the eye, obtain an angle corresponding to the power represented in the power information with reference to the angle relation information, and control the first mechanism based on the obtained angle to move the illumination system.

Further, in a sixteenth aspect of the present invention, in the stereomicroscope according to the second aspect, the second mechanism is configured to also move the head lens in an anteroposterior direction. The stereomicroscope further comprises: a storage configured to previously store distance relation information that relates a power of the head lens and a distance between the head lens and the objective lens; and a controller configured to receive power information of the head lens placed between the objective lens and the eye, obtain a distance corresponding to the power represented in the power information with reference to the distance relation information, and control the second mechanism based on the obtained distance to move the head lens in the anteroposterior direction.

Further, in a seventeenth aspect of the present invention, the stereomicroscope according to the second aspect further comprises: a storage configured to previously store displacement relation information that relates a power of the head lens and a displacement in the lateral direction of the optical axis of the head lens with respect to the optical axis of the objective lens; and a controller configured to receive power information of the head lens placed between the objective lens and the eye, obtain a displacement corresponding to the power represented in the power information with reference to the displacement relation information, and control the second mechanism based on the obtained displacement to move the head lens in the lateral direction.

Further, in an eighteenth aspect of the present invention, in the stereomicroscope according to the second aspect, the second mechanism includes a mount to which a plurality of head lenses having different powers are selectively mounted, and an indicator configured to indicate a position to mount each of the plurality of head lenses to the mount.

Further, in a nineteenth aspect of the present invention, in the stereomicroscope according to the first aspect, the first mechanism includes an indicator configured to indicate a position of the illumination system corresponding to each of a plurality of head lenses having different powers.

Further, in a twentieth aspect of the present invention, the stereomicroscope according to the first aspect further comprises a corrector configured to correct aberration caused in a state that the optical axis of the illumination system and the optical axis of the observation system are arranged so as to be nonparallel and the optical axis of the head lens and the optical axis of the objective lens are arranged so as to be separate in the lateral direction.

Effect of the Invention

The stereomicroscope according to the present invention acts so that, in intraocular observation of an eye, in a state that the optical axis of the illumination system and the optical axis of the observation system are arranged so as to be nonparallel and the optical axis of the head lens and the optical axis of the objective lens are arranged so as to be separate in the lateral direction, the illumination light emitted from the illumination system is caused to enter the inside of the eye via the head lens and the intraocularly reflected light of the illumination light is caused to enter the observation system via the head lens.

Since such a stereomicroscope is capable of letting out a light reflected by the head lens of the illumination light, it is possible to prevent occurrence of flare. Besides, since such a stereomicroscope enables intraocular observation using the illumination light propagated through the illumination diaphragm, it is possible to perform intraocular observation with a broader observation field than in using a slit light as conventional.

BRIEF DESCRIPTION OF THE DRAWINGS

FIG. 12 is a schematic view showing an example of a configuration of a modified example of the embodiment of the stereomicroscope (the slit lamp microscope) according to the present invention.

Figure 1:
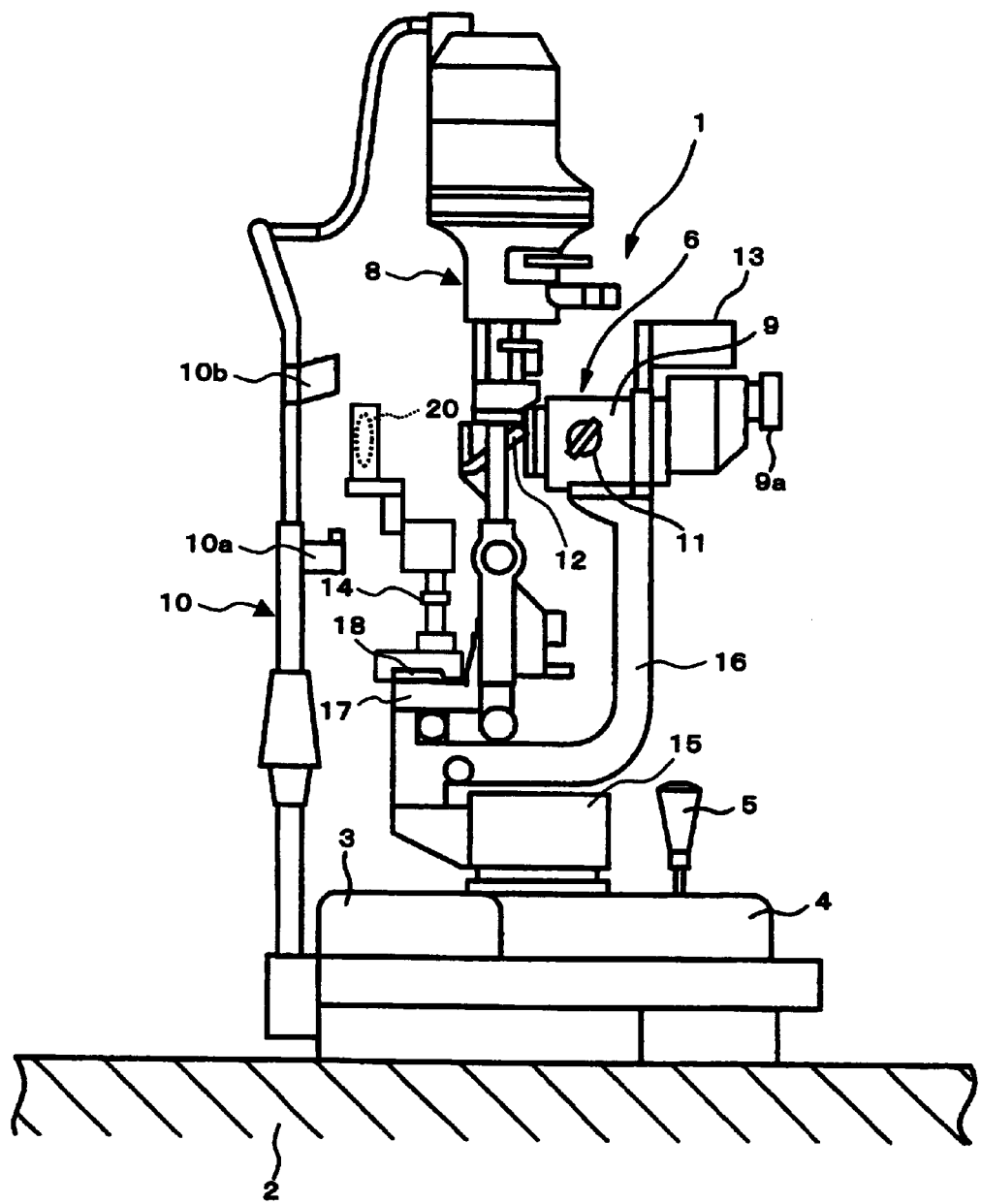
FIG. 1 is a schematic side view showing an example of an external configuration of an embodiment of a stereomicroscope (a slit lamp microscope) according to the present invention.

DESCRIPTION OF REFERENCE NUMERALS AND SYMBOLS 1 slit lamp microscope (stereomicroscope)
6 observation system
8 illumination system
14 head lens holder
20 head lens
31 objective lens
51 light source
56 illumination diaphragm
101 controller
102 storage
102a angle relation information
102b distance relation information
102c displacement relation information
104 manipulation part
105, 106 actuators
O1 observation optical axis
O2 illumination optical axis
OF head lens optical axis
E eye
Er fundus oculi

BEST MODE FOR CARRYING OUT THE INVENTION

An example of an embodiment of a stereomicroscope according to the present invention will be described in detail with reference to the drawings. In the following description, a slit lamp microscope will be described particularly in detail. However, by applying a configuration as in the following embodiment to other ophthalmologic stereomicroscopes (a surgical microscope and so on), it is also possible to obtain like actions and effects.

Directions used in the following description will be defined.

Firstly, a lateral direction will be a lateral direction when seen from an examiner (an operator). Therefore, in a binocular stereomicroscope according to this embodiment, a side on which an observation optical system for left eye exists is a "left direction", and a side on which an observation optical system for right eye exists is a "right direction". The lateral direction is defined as a horizontal direction. A vertical direction is a perpendicular direction orthogonal to the lateral direction. An anteroposterior direction is a direction orthogonal to both the lateral direction and the vertical direction. To be specific, since an examination using a slit lamp microscope is generally performed in a state that the examiner and the subject face each other, a direction from the examiner to the subject will be a forward direction. On the other hand, since an examination using a surgical microscope is performed on an eye of the subject lying on a bed, the anteroposterior direction will be an anteroposterior direction when seen from the examiner (the operator).

[External Configuration]

Firstly, an external configuration of the slit lamp microscope according to this embodiment will be described with reference to FIG. 1.

A slit lamp microscope 1 according to this embodiment is put on a table 2. A base 4 is configured to be capable of two-dimensionally moving in the horizontal direction via a movement mechanism part 3.

The base 4 is moved by tilting to manipulate a manipulation handle (a joystick) 5.

On the upper face of the base 4, a supporting part 15 that supports an observation system 6 and an illumination system 8 is mounted. To the supporting part 15, a supporting arm 16 that supports the observation system 6 is attached so as to be rotatable. On the supporting arm 16, a supporting arm 17 that supports the illumination system 8 is attached so as to be rotatable. The supporting arms 16 and 17 are configured to be independently rotatable around the same axis, respectively.

Of this rotation axis (not shown), a lower end is connected to the supporting part 15 and an upper end is connected to a mount 18.

It is possible to manually rotate the observation system 6 and the illumination system 8 by grasping the supporting arms 16 and 17, respectively. Moreover, the respective supporting arms 16 and 17 may be configured to be rotated by an electrical mechanism. In this case, an actuator that generates a driving force for rotating the respective supporting arms 16 and 17 and a transmission mechanism that transmits this driving force are disposed. The actuator is configured by, for example, a stepping motor (a pulse motor). The transmission mechanism is configured by, for example, a combination of gears, a rack and pinion, and so on.

The supporting arm 17 and aforementioned rotation axis for rotating the illumination system 8 configure examples of a "first mechanism" and a "rotation mechanism" of the present invention, respectively. Moreover, in a case that an electrical mechanism is applied, the actuator is also included in the first mechanism. The actuator functions as an example of a "first actuator" of the present invention.

On the mount 18, a head lens holder 14 that supports a head lens 20 for intraocular observation is mounted. The head lens holder 14 may be configured to be insertable into and removable from the mount 18.

Moreover, it is possible to fix the head lens holder 14 to the mount 18 to configure so that the head lens 20 can be retracted from a predetermined use position (a position between the observation system 6 and an eye).

It is possible to select one of the head lenses 20 having different powers and attach to the head lens holder 14. The head lenses 20 to be used have powers (refractive powers) about 40 diopter to 90 diopter.

One of the head lenses 20 is selected in accordance with, for example, the refractive power, axial length or the like of an eye.

The head lens holder 14 is provided with a mechanism for moving the head lens 20. To be specific, the head lens holder 14 can move the head lens 20 in the lateral direction. Preferably, the head lens holder 14 is configured to be capable of three-dimensionally moving the head lens holder 14. The head lens holder 14 is an example of a "second mechanism" of the present invention.

The head lens holder 14 is provided with a manipulation part such as a knob or a dial, and configured to move the head lens 20 in response to manual manipulation (rotation or the like) of the manipulation part. In the case of three-dimensionally moving the head lens 20, it is desirable to dispose a manipulation part for moving the head lens 20 in the lateral direction, the anteroposterior direction, and the vertical direction, respectively. Such a mechanism can be easily realized by using any known technique such as a rack and pinion.

The head lens holder 14 may include an electrical mechanism, instead of including the manual manipulation part as described above.

For example, the head lens holder 14 can be configured to move the head lens 20 by an actuator that generates a driving force and a transmission mechanism that transmits this driving force (a rack and pinion and the like). In a case that the head lens 20 is three-dimensionally moved, the actuator may be disposed for each direction, or a transmission mechanism for each direction may transmit a driving force from one actuator. Such an actuator is configured by a stepping motor or the like. The actuator disposed to the head lens holder 14 is an example of a "second actuator" of the present invention.

The illumination system 8 is provided with an optical system configured to project an illumination light to an eye. As mentioned above, the illumination system 8 can swing right and left around the rotation axis extending in the vertical direction, and can thereby change the projection direction of the illumination light with respect to an eye. Moreover, the illumination system 8 may be configured to be also capable of swinging up and down (that is to say, may be configured to be capable of changing an elevation angle and a depression angle of the illumination light).

The observation system 6 has a pair of optical systems on the right side and the left side that guide a light reflected by an eye of the illumination light (including various kinds of lights propagated through an eye, such as a scattered light). These optical systems are held in a lens barrel main body 9. As mentioned before, by rotating the supporting arm 16, it is possible to rotate the lens barrel main body 9 in the lateral direction, and it is thereby possible to change the direction of the observation system 6 with respect to an eye.

A jaw holder rack 10 is disposed in a position facing the lens barrel main body 9. The jaw holder rack 10 is provided with a jaw holder 10a and a forehead rest 10b for stably placing the face of the subject.

On a side face of the lens barrel main body 9, an observation magnification manipulation knob 11 for changing an observation magnification is disposed. Besides, to the lens barrel main body 9, an imaging apparatus 13 for imaging an eye is connected. The imaging apparatus 13 includes an imaging device such as a CCD image sensor or a CMOS image sensor. In a lower position of the illumination system 8, a mirror 12 configured to reflect an illumination light flux outputted from the illumination system 8 toward an eye is disposed.

[Configuration of Optical System]

Figure 2:
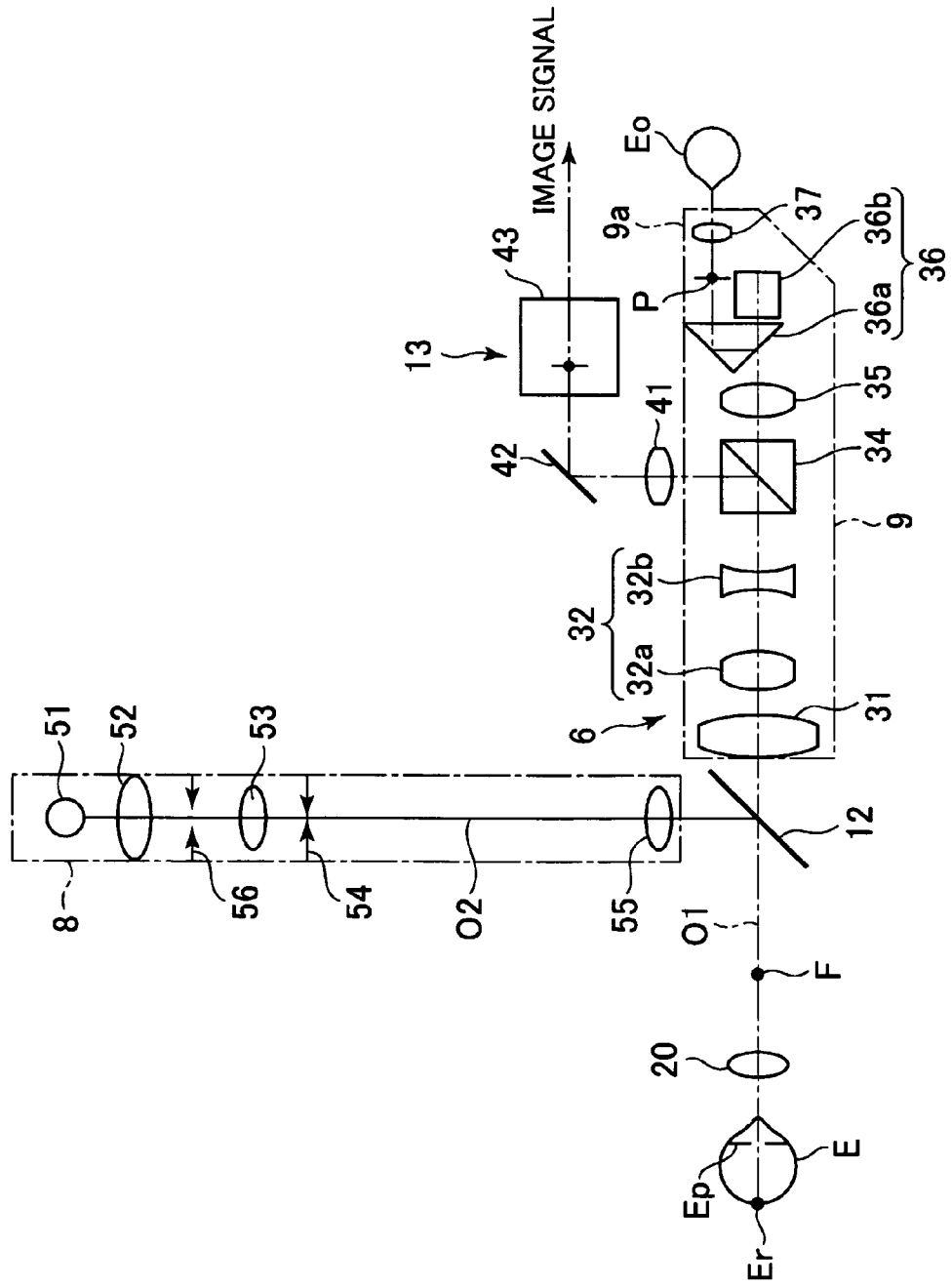
FIG. 2 is a schematic side view showing an example of a configuration of an optical system of the embodiment of the stereomicroscope (the slit lamp microscope) according to the present invention.

A configuration of an optical system of the slit lamp microscope 1 will be described with reference to FIG. 2. The optical system of the slit lamp microscope 1 includes the observation system 6 and the illumination system 8. The observation system 6 is provided with a pair of optical systems on the right side and the left side having almost the same configurations, which will be described in detail later. Thus, it is possible to binocularly observe an eye. An optical axis O1 of the observation system 6 will be identified with optical axes of the respective optical systems on the right side and the left side herein (they will be separated in FIGS. 6 and 7).

[Observation System]

The observation system 6 has an objective lens 31, a magnification optical system 32, a beam splitter 34, a relay lens 35, a prism 36, and an eyepiece lens 37. Symbol P denotes an imaging position of a light guided to the eyepiece lens 37. Symbol F denotes an imaging position of an inverted image of an intraocular site (fundus oculi Er or the like) of an eye E by the head lens 20. At the time of observation of an intraocular site, a focal position of the objective lens 31 and the imaging position F are caused to coincide with each other.

The magnification optical system 32 includes a plurality of (for example, two) magnification lenses 32a and 32b. By moving the respective lenses 32a and 32b along the observation optical axis O1, it is possible to change the magnification (the angle of view) of a macroscopic observation image and a captured image of the eye E. This magnification can be manually changed by manipulating the observation magnification manipulation knob 11. Alternatively, the magnification may be changed by electric power by manipulating a switch or the like that is not shown in the drawing.

The beam splitter 34 splits a light travelling along the observation optical axis O1 into two. The light transmitted through the beam splitter 34 is guided to an examiner's eye Eo via the relay lens 35, the prism 36 and the eyepiece lens 37. On the other hand, the light reflected by the beam splitter 34 is guided to an imaging device 43 of the imaging apparatus 13 via a relay lens 41 and a mirror 42. The imaging device 43 is configured by a CCD image sensor or a CMOS image sensor to detect the reflected light and generates an electric signal (an image signal). There is no need to provide both the right and left optical systems with the beam splitter 34.

[Illumination System]

The illumination system 8 has a light source 51, a relay lens 52, a condenser lens 53, a slit 54, and a condenser lens 55 as conventional.

These optical members are disposed along an illumination optical axis O2. The illumination system 8 may include a background illumination system for illuminating a region around an observation site of the cornea (refer to Japanese Unexamined Patent Application Publication No. 2005-224298, for example).

The light source 51 includes an optional light source device such as a halogen lamp or a xenon lamp. The illumination system 8 can be provided with a plurality of light sources. For example, it is possible to dispose a light source that outputs a continuous light and a light source that outputs a flash light. Alternatively, it is possible to separately dispose a light source for cornea observation and a light source for fundus oculi observation.

The slit 54 is used to generate a slit light for observing the cornea of the eye E. The slit 54 can be formed by a mechanism (a slitting part) disclosed in Japanese Unexamined Patent Application Publication No. 2005-224298, for example. The slit 54 is configured so that the size thereof (a slit width or the like) can be changed.

The illumination system 8 is provided with an illumination diaphragm 56 that interrupts part of the illumination light, in addition to the abovementioned configuration like a conventional one. In particular, the illumination diaphragm 56 effectively acts in observation of the fundus oculi Er. That is to say, the illumination diaphragm 56 has the following actions: (1) eliminate (reduce) reflection of the illumination light by the cornea and the crystalline lens; (2) change an aperture value to regulate luminance of illumination of the fundus oculi Er; and (3) change an aperture value to regulate a state of reflection of the illumination light on the surface or rear surface of the head lens 20 and inhibit flare.

[Configuration of Control System]

A control system of the slit lamp microscope 1 will be described with reference to FIG. 3. The control system of the slit lamp microscope 1 is configured so as to center on a controller 101. The controller 101 functions as an example of a "controller" of the present invention.

[Controller]

The controller 101 controls each part of the slit lamp microscope 1. For example, the controller 101 executes control of the operation of the observation system 6, control of the operation of the illumination system 8, and control of the imaging apparatus 13 (such as control of accumulation time, sensitivity or frame rate of the imaging device 43). Moreover, the controller 101 executes a process of reading out data stored in a storage 102, a process of writing data into the storage 102, and so on. Furthermore, the controller 101 executes various kinds of calculation processes.

The controller 101 includes a microprocessor, a RAM, a ROM, a hard disk drive, and so on. In this hard disk drive, a control program is previously stored. The controller 101 operates in accordance with this control program.

The controller 101 may be disposed within the housing (for example, within the base 4) of the slit lamp microscope 1, or may be disposed in a computer (not shown) connected to the slit lamp microscope 1.

[Storage]

The storage 102 stores various kinds of data used for the operation of the slit lamp microscope 1. Moreover, into the storage 102, data acquired by the slit lamp microscope 1 (such as image data obtained by imaging the eye E) is stored. The storage 102 may be placed within the housing (for example, within the base 4) of the slit lamp microscope 1, or may be placed in a computer (not shown) connected to the slit lamp microscope 1.

In the storage 102, specifically, angle relation information 102a, distance relation information 102b, and displacement relation information 102c are stored. The information 102a, 102b and 102c are previously generated and stored into the storage 102, respectively. The storage 102 is an example of a "storage" of the present invention.

(Angle Relation Information)

The angle relation information 102a is information that relates the power of the head lens 20 to the angle (the optical axis angle) of the illumination optical axis O2 with respect to the observation optical axis O1 (the optical axis of the objective lens 31).

As mentioned before, in this embodiment, it is possible to selectively use the head lenses 20 of various powers. In this case, as the angle relation information 102a, optical axis angles corresponding to the respective head lenses 20 are recorded.

The optical axis angle represents an angle between the observation optical axis O1 and the illumination optical axis O2 at which flare resulting from the head lens 20 does not occur. The illumination light outputted from the illumination system 8 enters the eye E via the head lens 20. At this moment, part of the illumination light is reflected on a boundary face (a refractive index boundary) between the head lens 20 and the air. A travelling direction of the reflected light varies depending on the optical axis angle. In a state that the optical axis angle is set within a predetermined range, the reflected light enters the observation system 6 and flare mixes into an observation image.

In this embodiment, it is sufficient that the reflected light does not enter, of the right and left optical systems of the observation system 6, the optical system on the same side as the illumination system 8. Accordingly, the optical axis angle in this embodiment is set to an angle at which the reflected light does not enter (at least) the optical system on the same side as the illumination system 8.

An optical axis angle corresponding to the head lens 20 having a certain power can be obtained by, for example, performing ray tracing on the assumption that the head lens 20 having the power is used. That is to say, while an angle between the observation optical axis O1 and the illumination optical axis O2 is varied, it is determined by ray tracing whether a light reflected on the surface or rear surface of the head lens 20 enters the observation system 6, and an angle (an optical axis angle) at which the reflected light does not enter the observation system 6 is thereby obtained.

In this case, it is assumed that the head lens 20 and the objective lens 31 are in a predetermined positional relation. As this positional relation, for example, it is possible to apply a state that the imaging position F of the head lens 20 and the focal position of the objective lens 31 are matched. Besides, the aperture value of the illumination diaphragm 56 is also assumed. Additionally, at the time of calculating the optical axis angle, it is possible to consider a displacement of the head lens 20 in the lateral direction (refer to a description of the displacement relation information 102c).

The angle relation information 102a is, for example, table information that relates each of the used head lenses 20 to an optical axis angle corresponding thereto. In this case, the angle relation information 102a is information that associates identification information of each of the head lenses 20 with the optical axis angle.

This identification information may be the power of the head lens 20, or may be string information (all these kinds of identification information will be referred to as a "power" generically). Alternatively, the angle relation information 102a may be graph information that represents a relation between the power and optical axis angle of the head lens 20.

The angle relation information 102a may be information that relates one value of the optical axis angle to the power of each of the head lenses 20, or may be information that relates the range of the optical axis angle to the power of each of the head lenses 20. In the latter case, it is desirable to previously determine a representative value of the range. As this representative value, for example, it is possible to set a value at the center of the range.

(Distance Relation Information)

The distance relation information 102b is information that relates the power of the head lens 20 to the distance (the lens distance) between the head lens 20 and the objective lens 31.

As mentioned before, when performing intraocular observation of the eye E, it is necessary to match the imaging position F of the head lens 20 and the focal position of the objective lens 31. The imaging position F, in other words, a distance between the head lens 20 and the imaging position F is determined based on the power of the head lens 20. On the other hand, a distance between the objective lens 31 and the focal point thereof is known. Therefore, by adding the distance from the head lens 20 to the imaging position F and the distance from the objective lens 31 to the focal position, it is possible to obtain a lens distance corresponding to the head lens 20.

Like the angle relation information 102a, the distance relation information 102b may be information that relates the identification information of the head lens 20 to the lens distance. Besides, instead of the lens distance, it is possible to use a position in the anteroposterior direction of the head lens 20 (this position is moved by the head lens holder 14). Since this position corresponds to the lens distance one by one, they can be identified.

(Displacement Relation Information)

The displacement relation information 102c is information that relates the power of the head lens 20 to a displacement (an optical axis displacement) in the lateral direction of the optical axis of the head lens 20 with respect to the observation optical axis O1 (the optical axis of the objective lens 31). The optical axis displacement represents such a displacement in the lateral direction of the optical axis of the head lens 20 with respect to the observation optical axis O1 that does not cause flare resulting from the head lens 20.

In general, in intraocular observation by a slit lamp microscope, the optical axis of the head lens 20 is matched with the observation optical axis O1 (that is to say, the head lens 20 is used coaxially with the observation system 6). On the other hand, the slit lamp microscope 1 according to this embodiment is featured by that flare resulting from the head lens 20 is prevented by making the head lens 20 eccentric with respect to the observation system 6, which will be described in detail later.

Like the angle relation information 102a, the displacement relation information 102c can be generated by performing ray tracing by assuming conditions such as the power of the head lens 20, the curvatures of both the lens surfaces, and the refractive index of the material.

It is desirable that both the displacement relation information 102c and the angle relation information 102a are associated with each other because both are factors that determine the travelling direction of the light reflected by the head lens 20. For example, for the illumination light and the intraocularly reflected light to pass through the head lens 20, the limit of the displacement amount in one direction of the head lens 20 is about half the lens diameter. Accordingly, by performing ray tracing while changing one or both of the displacement of the head lens 20 and the optical axis angle, it is possible to generate both the angle relation information 102a and the displacement relation information 102c.

Like the angle relation information 102a, the displacement relation information 102c may be such information that relates the identification information of the head lens 20 to the optical axis displacement.

[Display]

A display 103 displays various kinds of information under control by the controller 101. The display 103 includes any kind of display device such as a flat panel display like an LCD or a CRT display. The display 103 may be disposed to the housing (the examiner's side) of the slit lamp microscope 1, or may be disposed to a computer (not shown) connected to the slit lamp microscope 1.

[Manipulation Part]

A manipulation part 104 includes a manipulation device for manipulating the slit lamp microscope 1, and an input device for inputting information into the slit lamp microscope 1. For example, the manipulation part 104 includes a manipulation handle 5, a mouse and keyboard of the aforementioned computer, and so on. Moreover, it is possible to use any kind of manipulation device and input device, such as a track ball, a manipulation panel for exclusive use, a switch, a button and a dial. The manipulation part 104 functions as an example of a "manipulation part" of the present invention.

Figure 3:
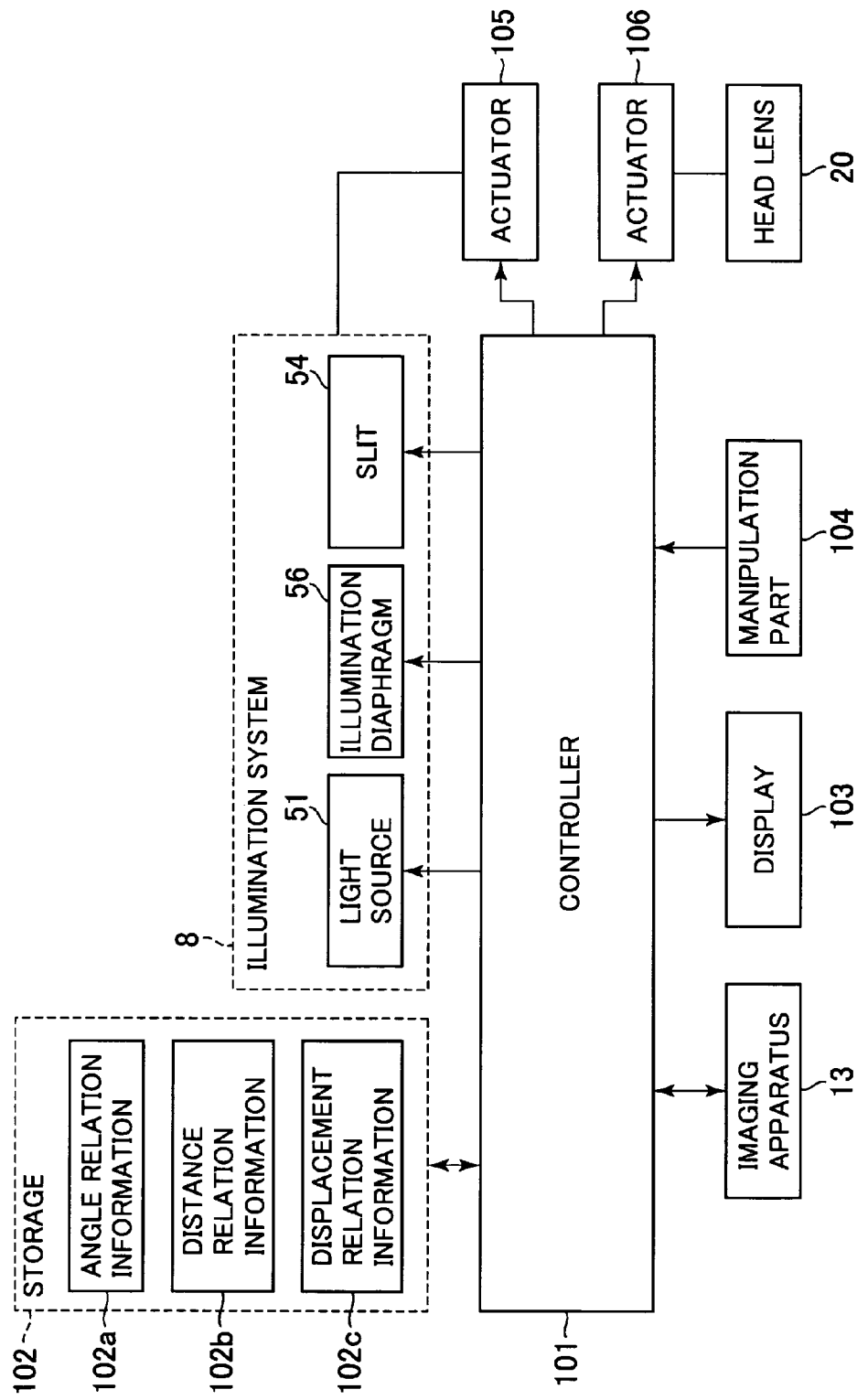
FIG. 3 is a schematic block diagram showing an example of a configuration of a control system of the embodiment of the stereomicroscope (the slit lamp microscope) according to the present invention.

In FIG. 3, the display 103 and the manipulation part 104 are shown separately, but can be configured in one body. As a specific example thereof, it is possible to use a touch-panel LCD.

[Actuator]

An actuator 105 is the actuator of the first mechanism for rotating the illumination system 8 (mentioned before). Moreover, an actuator 106 is the actuator of the second mechanism for moving the head lens 20 (mentioned before). The respective actuators 105 and 106 operate under control by the controller 101.

[Use Aspect]

Various use aspects of the slit lamp microscope 1 will be described. The slit lamp microscope 1 is used for both cornea observation and intraocular observation.

[Cornea Observation]

Cornea observation using the slit lamp microscope 1 will be described. The cornea observation is performed in a like manner as the conventional slit lamp microscope.

The head lens 20 is unnecessary for the cornea observation.

Moreover, the illumination diaphragm 56 is also unnecessary for the cornea observation. Therefore, in the cornea observation, the illumination diaphragm 56 is set open, for example. Alternatively, the illumination diaphragm 56 may be retracted from the optical axis O2 in the cornea observation. In this state, the cornea observation is executed in a like manner as conventional.

At the time of the cornea observation, firstly, alignment of the eye E and the observation system 6 is performed, and a slit-like illumination light (a slit light) is emitted to the eye E by the illumination system 8. This slit light is reflected and scattered on the cornea of the eye E.

This cornea reflected light (including the cornea scattered light) is guided to the right and left optical systems of the observation system 6 via the objective lens 31. Thus, the examiner can observe a cornea image of the eye E with both his/her eyes.

Further, part of the cornea reflected light reflected by the beam splitter 34 is detected by the imaging apparatus 13. Consequently, it is possible to acquire captured image data of the cornea of the eye E.

This image data is stored into the storage 102 as necessary.

[Fundus Oculi Observation]

The intraocular observation using the slit lamp microscope 1 will be described, taking observation of the fundus oculi Er as an example. Below, a case of manually performing an apparatus setup for the fundus oculi observation and a case of automatically switching the apparatus setup will be described.

(Case of Manually Switching Apparatus Setup)

Figure 4:
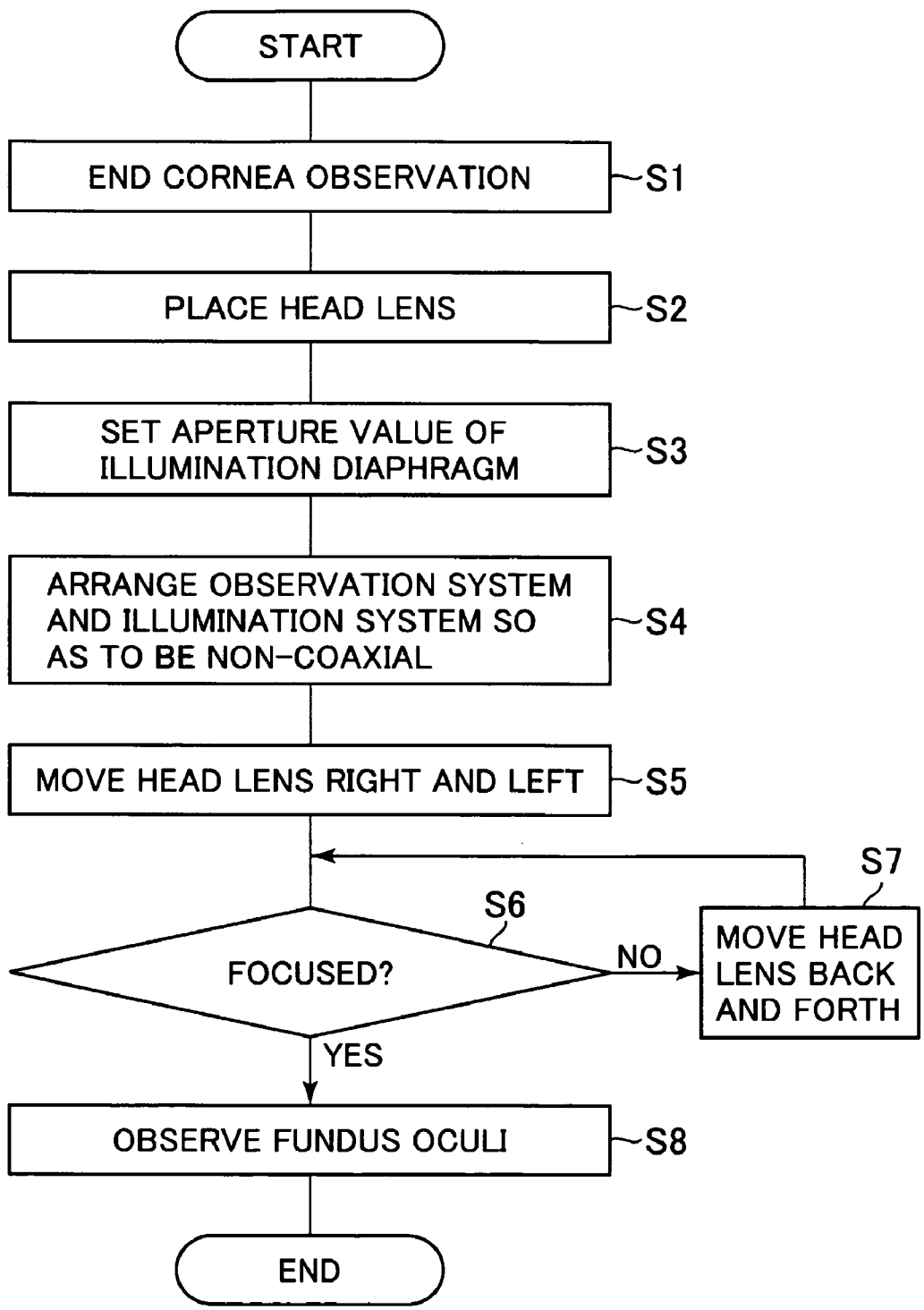
FIG. 4 is a flow chart showing an example of a use aspect of the embodiment of the stereomicroscope (the slit lamp microscope) according to the present invention.

A use aspect in the case of manually switching to the apparatus setup for the fundus oculi observation will be described. A flow chart of FIG. 4 shows an example of the use aspect in this case.

When the cornea observation of the eye E is ended (S1), the examiner places the head lens 20 between the eye E and the objective lens 31 (S2). For this, for example, the examiner mounts the head lens 20 on the head lens holder 14, and mounts the head lens holder 14 to the mount 18. At this stage, the head lens 20 is placed coaxially with the observation optical axis O1.

The examiner manipulates the manipulation part 104 to set the aperture value of the illumination diaphragm 56 (S3). At this moment, the examiner opens the slit 54 by manipulating the manipulation part 104, for example.

The examiner moves the illumination system 8 to arrange the observation system 6 and the illumination system 8 so as to be non-coaxial (nonparallel). The examiner performs this manipulation by, for example, grasping the supporting arm 17. Alternatively, the examiner may manipulate the manipulation part 104 so that, in response to the manipulation, the controller 101 controls the actuator 105 to move the illumination system 8.

Figure 5:
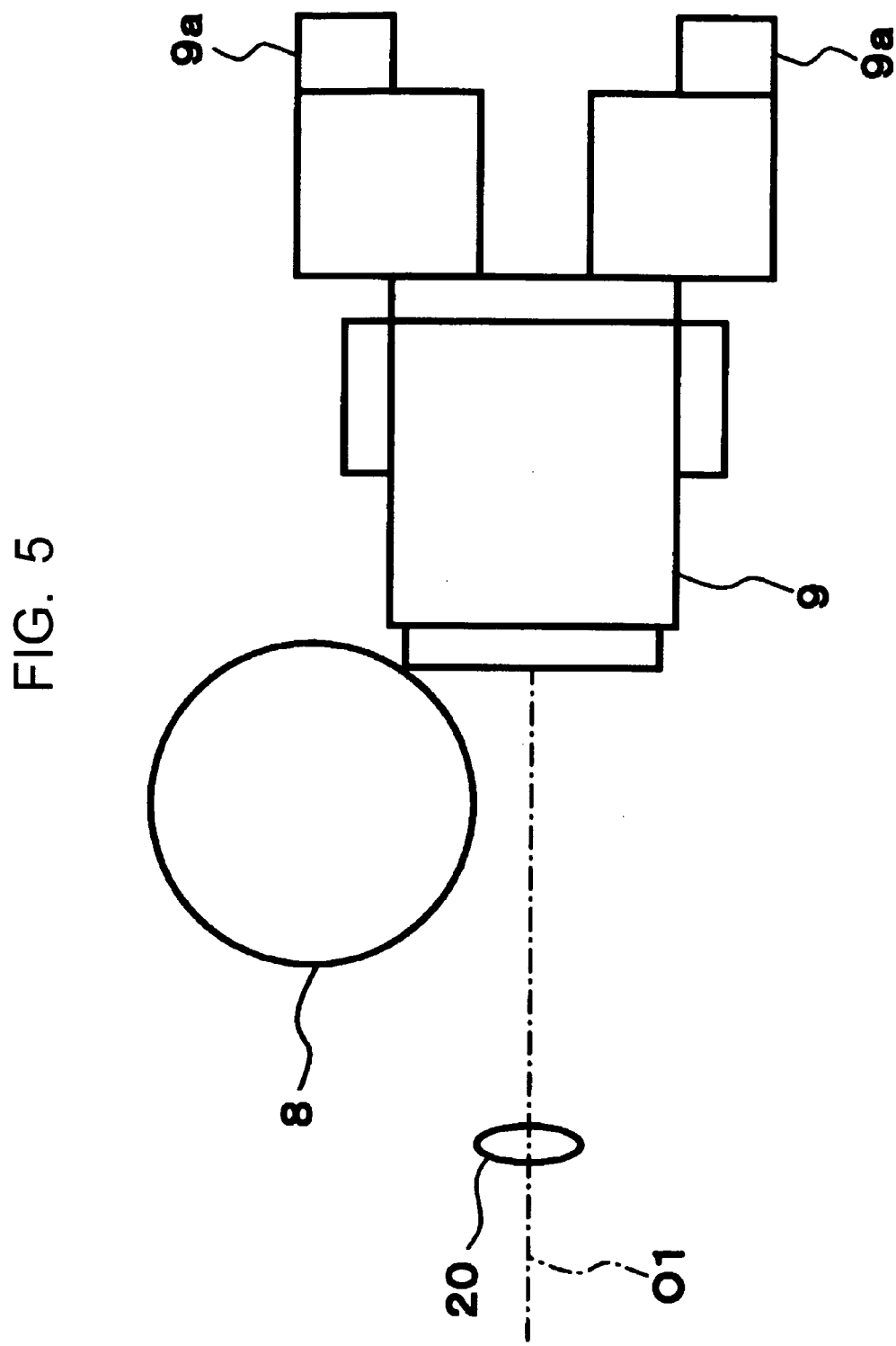
FIG. 5 is a schematic top view showing an example of the external configuration of the embodiment of the stereomicroscope (the slit lamp microscope) according to the present invention.
Figure 6:
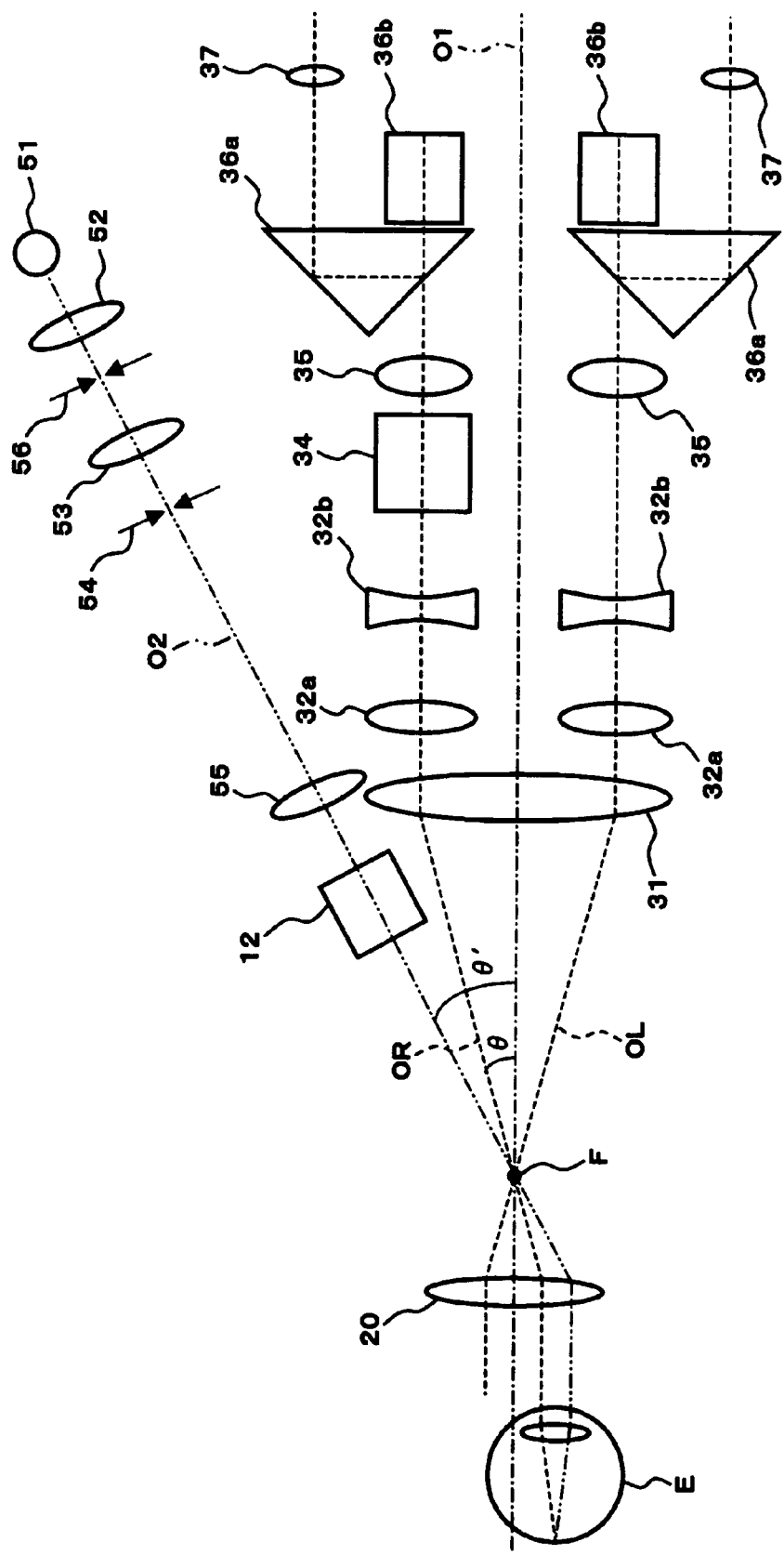
FIG. 6 is a schematic top view showing an example of the configuration of the optical system of the embodiment of the stereomicroscope (the slit lamp microscope) according to the present invention.

A state that the observation system 6 and the illumination system 8 are arranged so as to be non-coaxial is shown in FIGS. 5 and 6.

In this arrangement state, the illumination system 8 is arranged on the right side of the observation optical axis O1. Symbols OR and OL shown in FIG. 6 denote the optical axes of the right and left optical systems of the observation system 6, respectively (referred to as the right observation optical axis OR and the left observation optical axis OL, respectively).

An angle between the observation optical axis O1 and the right observation optical axis OR is denoted by θ, and an angle between the observation optical axis O1 and the illumination optical axis O2 is denoted by θ'. An angle between the observation optical axis O1 and the left observation optical axis OL is denoted by −θ (with reference to the observation optical axis O1, the counterclockwise direction is defined as the positive direction and the clockwise direction is defined as the negative direction).

The examiner moves the head lens 20 in the lateral direction (S5). For this, the examiner manually manipulates the manipulation part of the head lens holder 14. Alternatively, the examiner may manipulate the manipulation part 104 so that, in response to the manipulation, the controller 101 controls the actuator 106 to move the head lens 20. The head lens 20 is moved in the same direction as the illumination system 8. In the case shown in FIGS. 5 and 6, the head lens 20 is moved in the right direction.

Figure 7:
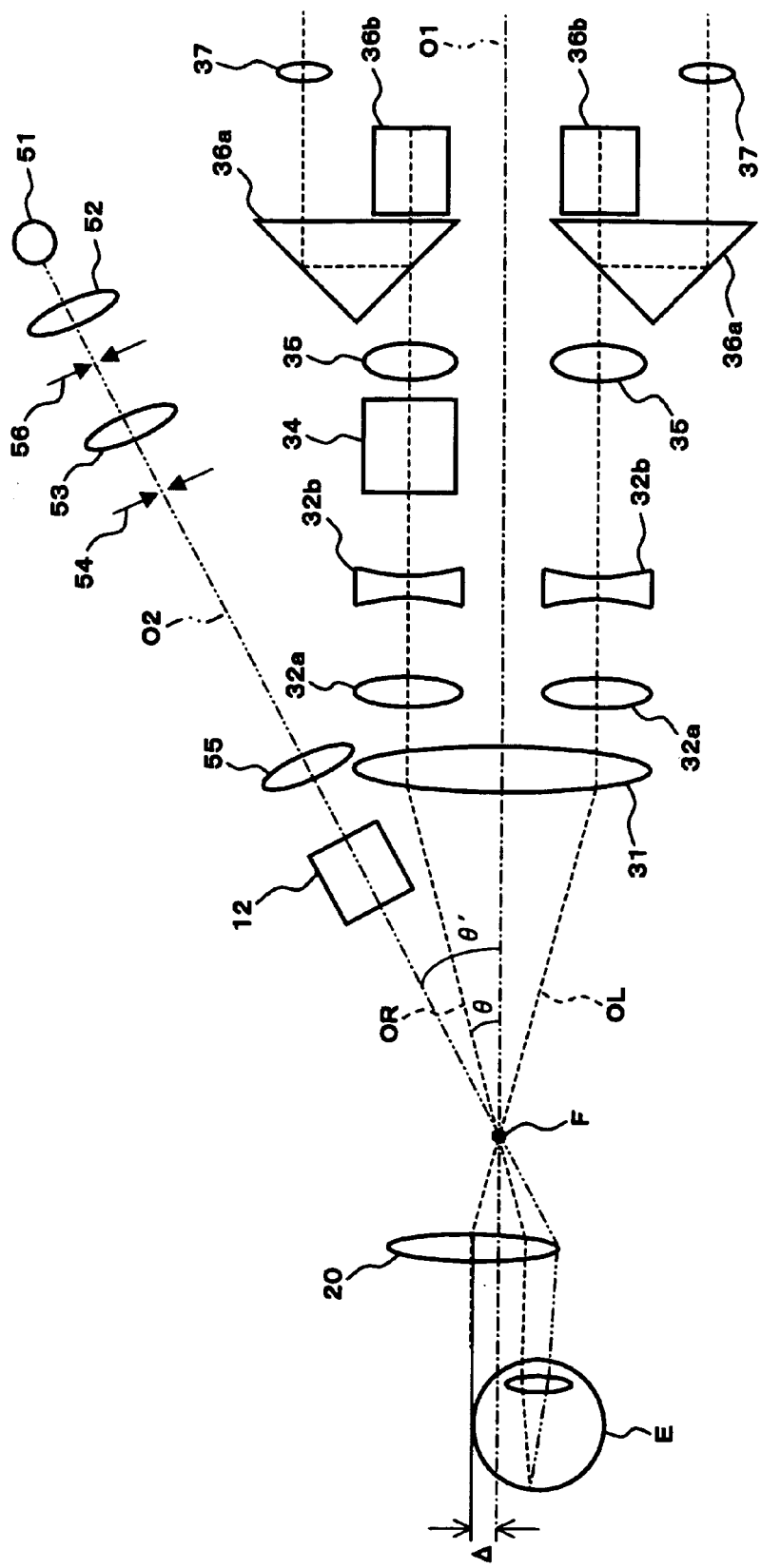
FIG. 7 is a schematic top view showing an example of the configuration of the optical system of the embodiment of the stereomicroscope (the slit lamp microscope) according to the present invention.

An arrangement state of the optical system after movement of the head lens 20 is shown in FIG. 7. A displacement of an optical axis (a head lens optical axis) OF of the head lens 20 with respect to the observation optical axis O1 is denoted by symbol Δ.

Figure 8:
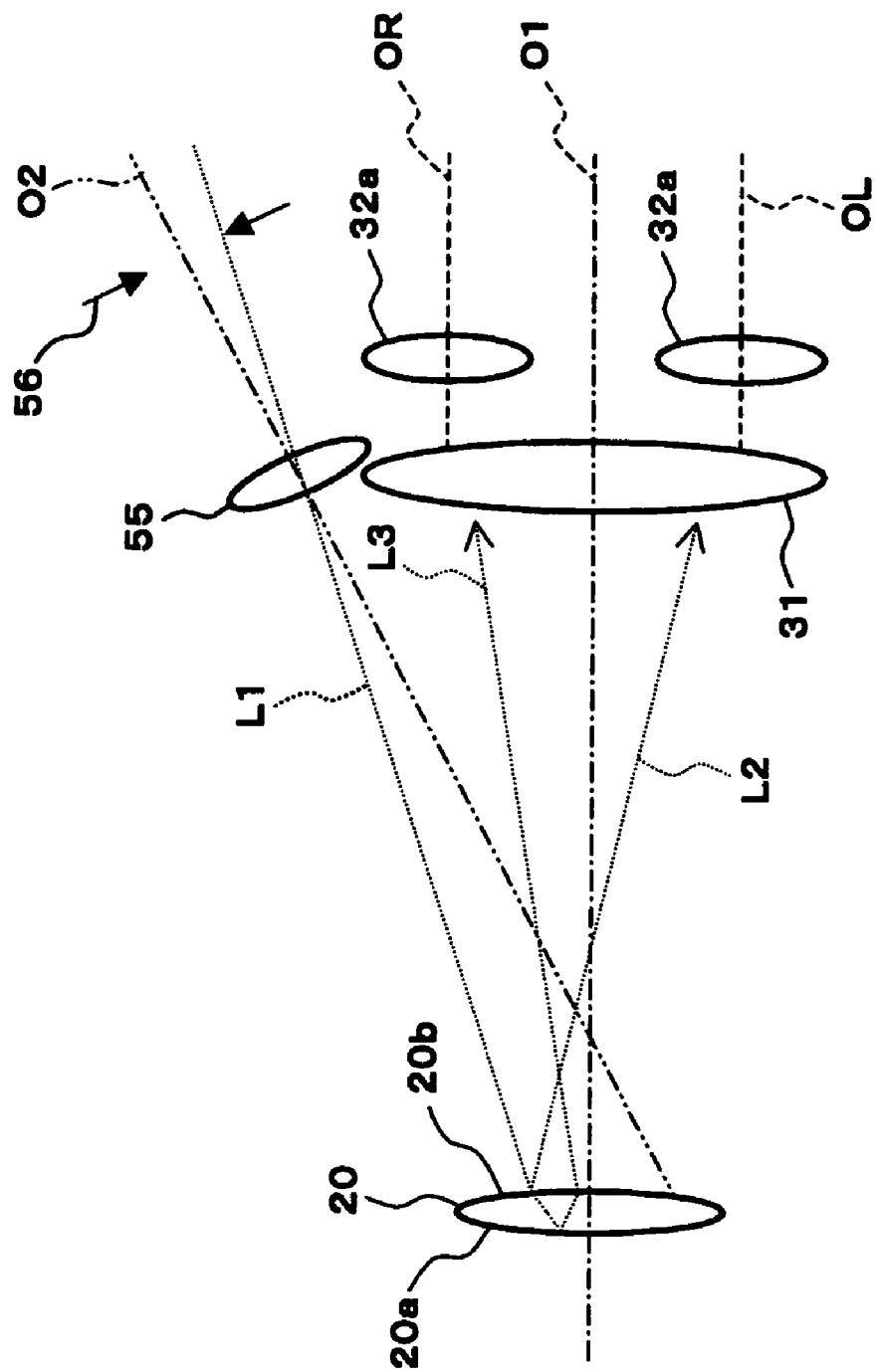
FIG. 8 is a schematic top view for explaining an example of the use aspect of the embodiment of the stereomicroscope (the slit lamp microscope) according to the present invention.
Figure 9:
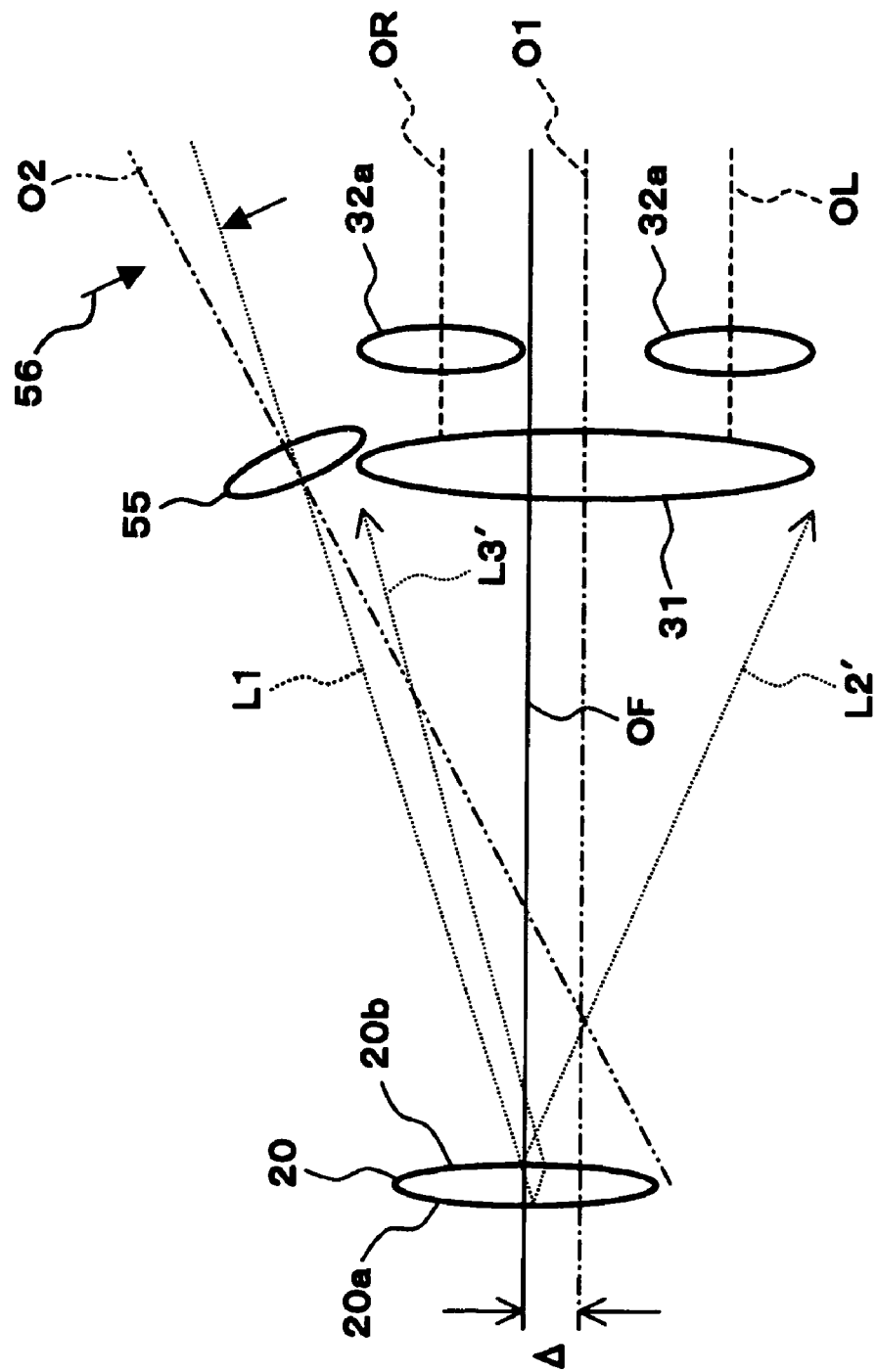
FIG. 9 is a schematic top view for explaining an example of the use aspect of the embodiment of the stereomicroscope (the slit lamp microscope) according to the present invention.

With reference to FIGS. 8 and 9, a reason for moving the head lens 20 in the lateral direction will be described. FIG. 8 shows an arrangement state before the head lens 20 is moved, namely, an arrangement state shown in FIG. 6. FIG. 9 shows an arrangement state after the head lens 20 is moved by Δ, namely, an arrangement state shown in FIG. 7.

Before the head lens 20 is moved, a light L1 passed through an aperture end of the illumination diaphragm 56 is partially reflected by a rear surface 20b (a lens face closer to the objective lens 31) of the head lens 20. This reflected light L2 travels toward the objective lens 31. Moreover, the light L1 transmitted through the rear surface 20b is partially reflected by a surface 20a. This reflected light L3 travels toward the objective lens 31. Thus, before the head lens 20 is moved, the light reflected by the head lens 20 enters the right and left optical systems (especially, the right optical system) via the objective lens 31, with the result that flare mixes in an observation image.

On the other hand, after the head lens 20 is moved, of the light L1 passed through the aperture end of the illumination diaphragm 56, a reflected light L2' by the rear surface 20b of the head lens 20 passes outside (the left side of) the objective lens 31. Moreover, a reflected light L3' by the surface 20a also passes outside (the right side of) the objective lens 31. Thus, after the head lens 20 is moved, the light reflected by the head lens 20 does not enter either the right or left optical systems (especially, the right optical system), with the result that flare resulting from the head lens 20 will not mix in an observation image.

In a case that flare mixes in an observation image after movement of the head lens 20, the examiner can regulate the position of the head lens 20 and the optical axis angle θ' while referring to the observation image of the fundus oculi Er, thereby seeking a favorable arrangement state as shown in FIG. 9.

The examiner moves the head lens 20 in the anteroposterior direction to focus with respect to the fundus oculi Er when necessary (S6, S7).

When the preparation described above ends, the examiner looks through the eyepiece lens 37 to observe a magnified image of the fundus oculi Er (S8).

In the case of applying the arrangement of the optical systems as described above, as shown in FIG. 7, a reflected light by the fundus oculi Er enters only the optical system on the side of the illumination system 8 (on the right side), of the right and left optical systems of the observation system 6. Therefore, it is desirable that the examiner performs the fundus oculi observation with his/her left eye closed.

Alternatively, the optical path of the left optical system may be interrupted so that a light having entered the left optical system is interrupted. The optical path can be interrupted by using any kind of member (an interrupting part) such as a diaphragm or a shutter.

(Case of Automatically Switching Apparatus Setup)

Figure 10:
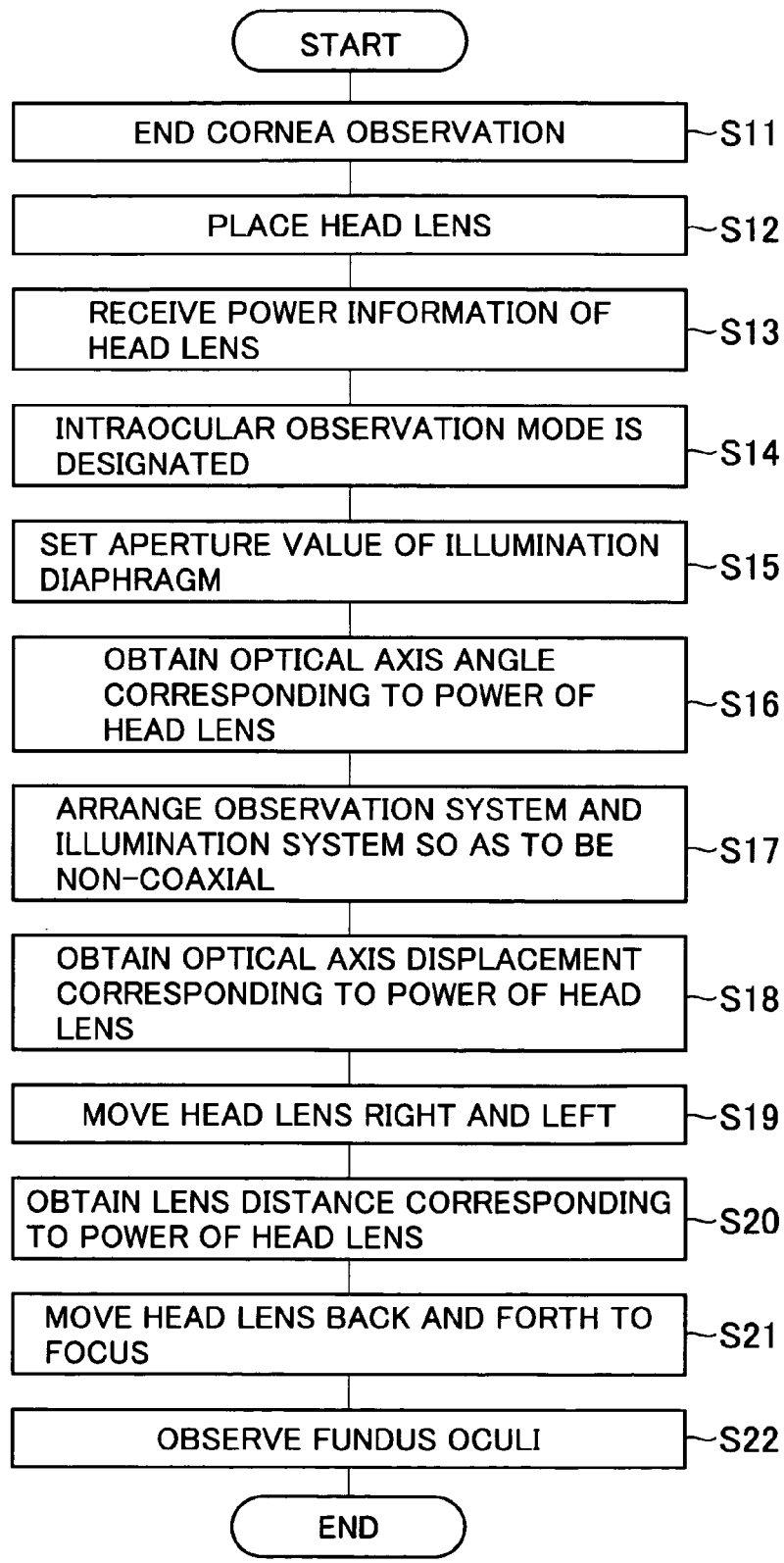
FIG. 10 is a flow chart showing an example of the use aspect of the embodiment of the stereomicroscope (the slit lamp microscope) according to the present invention.

A use aspect in the case of automatically switching to the apparatus setup for the fundus oculi observation will be described. A flow chart of FIG. 10 shows an example of the use aspect in this case.

When the cornea observation of the eye E ends (S11), the head lens 20 is placed between the eye E and the objective lens 31 (S12).

The operation of placing the head lens 20 may be manually performed by the examiner, or may be performed by control of the head lens holder 14 by the controller 101.

The controller 101 receives power information of the head lens 20 to be used (S13). For example, this power information is sent to the controller 101 by inputting the power (or the identification information) of the head lens 20 to be used with the manipulation part 104. Alternatively it is possible to configure so that each of the head lenses 20 is given unique information and the controller 101 acquires the power information by automatically reading this unique information.

The examiner manipulates the manipulation part 104 to designate an intraocular observation mode (S14). In this case, a fundus oculi observation mode for observing the fundus oculi Er is designated.

An observation mode represents the setup of each part and operation aspect of the slit lamp microscope 1 for observing a predetermined site (cornea, fundus oculi, and so on) of an eye.

When the fundus oculi observation mode is designated, the controller 101 controls the illumination diaphragm 56 to set an aperture value (S51). In this case, the aperture value may be set with reference to the power information of the head lens 20 obtained at step 13. The relation between the power information and the aperture value is previously generated and stored into the storage 102, for example, like the aforementioned angle relation information 102a. Moreover, the controller 101 controls the slit 54 to be kept open.

Based on the power information of the head lens 20 and the angle relation information 102a, the controller 101 obtains an optical axis angle corresponding to a power represented in the power information (S16). Furthermore, based on this optical axis angle, the controller 101 controls the actuator 105 to move the illumination system 8, thereby arranging the observation system 6 and the illumination system 8 so as to be non-coaxial (nonparallel) (S17).

Consequently, the observation system 6 and the illumination system 8 are arranged so that the optical axes O1 and O2 form the optical axis angle (refer to FIGS. 5 and 6).

The controller 101, based on the power information of the head lens 20 and the displacement relation information 102c, obtains a displacement (the optical axis displacement Δ) in the lateral direction of the head lens 20 corresponding to the power represented in the power information (S18). Furthermore, the controller 101 controls the actuator 106 based on this optical axis displacement Δ to move the head lens 20 in the lateral direction (S19). Consequently, the head lens optical axis OF and the observation optical axis O1 are brought into a state separated by distance Δ (refer to FIG. 7).

Before the head lens 20 is moved, the head lens optical axis OF and the observation optical axis O1 shall match. Alternatively, for example, the apparatus may be configured to be capable of detecting the position of the head lens 20 based on the state of the head lens holder 14 (the actuator) to thereby move the head lens 20 to a target position while monitoring a positional relation between the head lens optical axis OF and the observation optical axis O1. The position of the head lens 20 can also be detected by using another part such as a potentiometer.

The controller 101 obtains a distance (a lens distance) between the head lens 20 and the objective lens 31 based on the power information of the head lens 20 and the distance relation information 102b (S20). Furthermore, the controller 101 controls the actuator 106 based on this lens distance to move the head lens 20 in the anteroposterior direction and focus with respect to the fundus oculi Er (S21).

When the preparation described above ends, the examiner looks through the eyepiece lens 37 to observe a magnified image of the fundus oculi Er (S22).

In this embodiment, as shown in FIG. 7, a reflection light by the fundus oculi Er enters only the optical system on the side of the illumination system 8 (on the right side), of the right and left optical systems of the observation system 6. Therefore, it is desirable that the examiner performs the fundus oculi observation with his/her left eye closed. Alternatively, the optical path of the left optical system may be interrupted so that a light having entered the left optical system is interrupted. The optical path can be interrupted by using any kind of member (an interrupting part) such as a diaphragm or a shutter.

[Other Use Aspect]

Although various kinds of setups for intraocular observation of the eye E are automatically switched in the use aspect shown in FIG. 10, one or more of the setups may be manually switched. That is to say, although control of the aperture value of the illumination diaphragm 56, control of the operation of opening the slit 54, control of changing the optical axis angle, control of changing the optical axis displacement, control of changing the lens distance, and so on are automatically performed in the abovementioned use aspect, any of these setups can be manually performed. The case of manually setting has already been described in the use aspect shown in FIG. 4.

Further, it is possible to manually regulate a state having been automatically set in the use aspect shown in FIG. 10 as necessary.

Further, although the optical axis angle, the optical axis displacement and the lens distance are obtained based on the power of the head lens 20, respectively, in the use aspect shown in FIG. 10, part of these conditions may be kept constant regardless of the power and the remaining conditions may be obtained based on the power. At the time of obtaining the remaining conditions, the part of the conditions is also taken into consideration (that is to say, the part of the conditions is reflected on information generated in advance).

Although a case of shifting from the anterior segment (cornea) observation mode to the intraocular (fundus oculi) observation mode in the above use aspect, on the contrary, it is also possible to perform a like process in the case of shifting from the intraocular observation mode to the anterior segment observation mode.

In the case of manually shifting from the intraocular observation mode to the anterior segment observation mode, a reverse process from the use aspect shown in FIG. 4 is performed. For example, the examiner can cause the head lens 20 to retract from a position between the eye E and the objective lens 31, make the illumination diaphragm 56 open, change the optical axis angle as necessary, and change the position of the head lens 20 in the lateral direction and the anteroposterior direction as necessary. Moreover, the examiner can also regulate the size (the slit width or the like) of the slit 54 as necessary.

Further, in the case of automatically shifting from the intraocular observation mode to the anterior segment observation mode, a reverse process from the use aspect shown in FIG. 10 is executed. For example, the controller 101 can cause the head lens 20 to retract, make the illumination diaphragm 56 open, change the optical axis angle to a predetermined default value, and change the position of the head lens 20 in the lateral direction and the anteroposterior direction to a predetermined default position. Moreover, the controller 101 also can change the size (the slit width or the like) of the slit 54 to a predetermined default value (a slit size for the cornea observation).

One or more of these controls may be manually performed.

[Actions and Effects]

Actions and effects of the slit lamp microscope 1 according to this embodiment will be described.

In intraocular observation of the eye E (the fundus oculi Er and so on), the slit lamp microscope 1 acts to make an illumination light emitted from the illumination system 8 enter the inside of the eye E via the head lens 20 and make the intraocularly reflected light of the illumination light enter the observation system 6 via the head lens 20 in a state that the observation optical axis O1 and the illumination optical axis O2 are arranged so as to be nonparallel and the head lens optical axis OF and the optical axis of the objective lens 31 (the observation optical axis O1) are arranged so as to be separated in the lateral direction.

According to the slit lamp microscope 1 as described above, it is possible to let the light reflected by the head hens 20 of the illumination light outside the observation system 6 as shown in FIG. 9, so that it is possible to prevent occurrence of flare.

In addition, according to the slit lamp microscope 1, it is possible to perform intraocular observation by using the illumination light propagated through the illumination diaphragm 56, so that it is possible to perform intraocular observation with a broader observation field than an observation field by a slit light as conventional. Since the aperture value of the illumination diaphragm 56 can be set to a maximum aperture value that reflection by the head lens 20 of the illumination light does not occur and vignetting of the illumination light by the pupil of the eye E does not occur, it is possible to obtain a sufficiently broader observation field than an observation field by a conventional slit light.

For example, an observation field by a conventional slit light is a rectangular region of about 6°×18° in angle of view, but it is possible to obtain a circular observation field of about 30° in angle of view according to this embodiment. That is to say, what can be observed in one observation is, for example, only the optic papilla and neighborhood thereof of the fundus oculi Er in the conventional observation field, but it is possible to observe a broad range including the optical papilla and the macula in one observation according to this embodiment.

Further, the slit lamp microscope 1 is configured to, in intraocular observation of the eye E, make the intraocularly reflected light enter the right (left) optical system of the observation system 6 in a state that the illumination system 8 is arranged on the right (left) side of the observation system 6 and the head lens optical axis OF is arranged on the right (left) side of the optical axis O1 of the objective lens 31 (refer to FIG. 7).

Conventionally, intraocular observation has been generally performed with both the right and left optical systems. This has been enabled by the small observation field. On the other hand, this embodiment enables observation of a broad range by guiding the intraocularly reflected light to one of the right and left optical systems.

Accordingly, the examiner can observe a broad intraocular range with one eye.

For the observation with one eye, it is desirable that the examiner closes the other eye in order to avoid viewing a light entering the other optical system. In order to avoid such bother, the slit lamp microscope 1 is capable of interrupting the light having entered the other optical system with an interrupting part.

Considering reflection by the head lens 20 and vignetting by the pupil, the breadth of an observation field and whether or not to observe with both eyes are in the tradeoff relation. An object of this embodiment is to obtain a broad observation field without causing flare.

However, it is possible to perform observation with both eyes by using the slit lamp microscope 1. In this case, there is a need to set the aperture of the illumination diaphragm 56 small enough, or use the slit 54.

Further, the slit lamp microscope 1 acts to obtain an optical axis angle corresponding to the power of the used head lens 20 with reference to the angle relation information 102a and, based on this optical axis angle, move the illumination system 8. Consequently, it is possible to easily set a favorable optical axis angle (the angle between the observation optical axis O1 and the illumination optical axis O2) for intraocular observation.

Further, the slit lamp microscope 1 is capable of obtaining a lens distance corresponding to the power of the used head lens 20 with reference to the distance relation information 102b and, based on this lens distance, move the head lens 20 in the anteroposterior direction to focus. Consequently, it is possible to easily focus with respect to an intraocular site to be observed.

The focusing can be executed in a like manner as the automatic focus function of general cameras. Alternatively, it is possible to automatically focus by changing a distance between the head lens 20 and the objective lens 31 while analyzing an image captured by the imaging apparatus 13. Alternatively, it is also possible to configure to be capable of moving the observation system 6 in the anteroposterior direction with respect to the head lens 20.

Further, the slit lamp microscope 1 acts to obtain an optical axis displacement corresponding to the power of the used head lens 20 with reference to the displacement relation information 102c and, based on this optical axis displacement, move the head lens 20 in the lateral direction. Consequently, it is possible to easily set a favorable optical axis displacement (an interval between the observation optical axis O1 and the head lens optical axis OF) for intraocular observation.

Modified Example

The configuration described above is merely a specific example for embodying the present invention. Those who intend to embody the present invention can make any modification within the scope of the present invention as necessary. Below, examples of the modification will be described.

Modified Example 1

Figure 11:
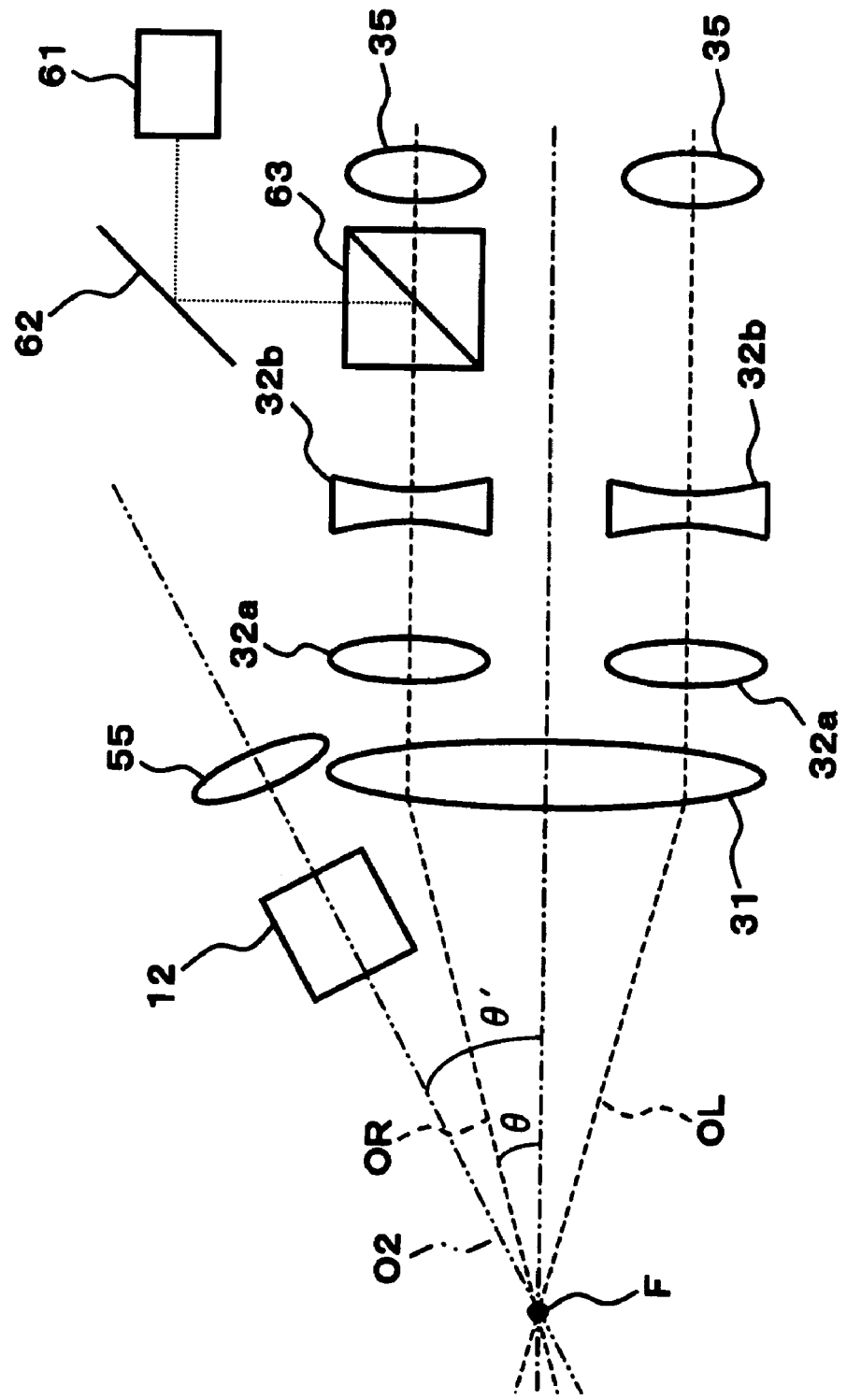
FIG. 11 is a schematic top view showing an example of a configuration of an optical system of a modified example of the embodiment of the stereomicroscope (the slit lamp microscope) according to the present invention.

A modified example of the embodiment described above will be shown in FIG. 11. In this modified example, a fixing optical system that projects a fixation target to an eye is disposed to the observation system 6. The fixing optical system is specifically disposed to an optical system that guides the intraocularly reflected light of the illumination light. For performing intraocular observation by switching the right and left optical systems, both the right and left optical systems are provided with the fixing optical systems, respectively. The fixing optical system is an example of a "projector" of the present invention.

The fixing optical system includes, for example, a fixation target presenting part 61, a reflection mirror 62, and a beam splitter 63.

The fixation target presenting part 61 presents a fixation target.

The fixation target presenting part 61 includes a flat panel display such as an LCD, a lens, and so on. This flat panel display can display a fixation target at various positions on a display screen by control of the controller 101. Other than the flat display panel, it is possible to employ, for example, the fixation target presenting part 61 in which a plurality of LEDs selectively turned on by the controller 101 are arranged.

A light flux (a fixation target) outputted from the fixation target presenting part 61 is reflected by the reflection mirror 62 and guided to the beam splitter 63. The beam splitter 63 reflects this light flux and causes the light flux to travel toward the objective lens 31 along the optical axis OR. This light flux enters the eye E via the objective lens 31 and the head lens 20 and is projected to the fundus oculi Er (not shown in the drawing).

The examiner gives a subject an instruction to stare this fixation target. By changing a position to present the fixation target by the fixation target presenting part 61, it is possible to make the eye E fix in various directions. Consequently, it is possible to change an intraocular site to be observed. For example, it is possible to observe the fundus oculi Er with an observation field about the optic papilla, observe the fundus oculi Er with an observation field about the macula, or observe the fundus oculi Er with an observation field about a lesion site.

It is also possible to dispose a fixation lamp (an external fixation lamp) to the outside of the housing of the apparatus to fix the eye E.

Modified Example 2

In the embodiment described above, by moving the head lens 20 in the lateral direction, the optical axis of the head lens 20 and the optical axis of the objective lens 31 are arranged so as to be separate from each other. This modification example will describe a configuration example to arrange the optical axis of the head lens 20 and the optical axis of the objective lens 31 so as to be separate by changing a position to mount the head lens 20 on the head lens holder 14.

Although it is not necessary to dispose a mechanism for moving the head lens 20 in the lateral direction in the stereomicroscope according to this modified example, it is desirable to dispose the mechanism for the purpose of, for example, performing minute adjustment of the position of the head lens 20, or inserting/retracting the head lens 20 into/from the optical path.

FIG. 12 shows a configuration of the stereomicroscope according to this modified example. FIG. 12 is a view taken from the front (or the rear) of the head lens 20 and the head lens holder 14.

The head lens 20 is set in a lens frame 21. To the lens frame 21, a mount 22 for mounting the head lens holder 14 is attached. It is also possible to configure the lens frame 21 and the mount 22 in one body.

The aspects of the lens frame 21 and the mount 22 are arbitrary.

To the top end of the head lens holder 14, a mount 14a is disposed. On the top end of the mount 14a, a groove is formed along the lateral direction (not shown in the drawing). One end in the longitudinal direction of the mount 22 for the head lens 20 is connected to the lens frame 21, and the other end is inserted into the groove of the head lens holder 14. The groove acts to hold the mount 22. Thus, the head lens 20 is mounted on the head lens holder 14. It is also possible to dispose a member (a screw, an elastic member or the like) for holding the mount 22 so that the mount 22 inserted in the groove does not move.

To the head lens holder 14, a plurality of head lenses 20 having different powers are selectively mounted. As mentioned before, the head lens 20 is arranged off the observation optical axis O1 in the lateral direction and used for intraocular observation. The head lens holder 14 is provided with an indicator 14b that indicates the positions to mount the respective head lenses 20 to the mount 14a.

The indicator 14b includes identification information of the head lens 20 and mounting position information. Symbols I, II and III shown in FIG. 12 denote examples of the identification information.

The identification information may be the power of the head lens 20. Moreover, the mounting position information is a line (a dotted line in FIG. 12) extending from the identification information to the top end of the mount 14a.

The identification information and the mounting position information are given on both the sides in the lateral direction in consideration of both mounting the head lens 20 on the left side of the observation optical axis O1 and mounting the head lens 20 on the right side (that is, in consideration of both arranging the illumination system 8 on the left side and arranging the illumination system 8 on the right side, in other words, both observing with the left optical system of the observation system 6 and observing with the right optical system). In the case of applying only one of the sides, it is sufficient to dispose the indicator 14b only to the corresponding side.

According to this modified example, it is possible to easily mount the head lens 20 in a favorable position. The mount 14a is an example of a "mount" of the present invention. The indicator 14b is an example of an "indicator" of the present invention.

Even when the head lens holder 14 enables the head lens 20 to move in the lateral direction, it is possible to dispose the indicator. To be specific, in a case that the examiner manipulates the manipulation part 104 to move the head lens 20 with electric power, the examiner moves the head lens 20 to a position indicated by the indicator, thereby being capable of easily arranging the head lens 20 in a favorable position.

Further, the indicator can be adapted in order to determine the position (the optical axis angle) of the illumination system 8. For example, by disposing an indicator that indicates the position (the optical axis angle) of the illumination system 8 corresponding to each of the plurality of head lenses having different powers, to a first mechanism (supporting arm 17 and neighborhood positions), it is possible to easily set the optical axis angle. This indicator is formed by providing scales and letters to a position corresponding to a trajectory (arch-like) of the illumination system 8.

Modified Example 3

In intraocular observation described in the embodiment described above, a prism effect is caused by movement of the head lens 20 in the lateral direction, and an observation image is affected by aberration. In order to solve such aberration, it is possible to dispose a part configured to correct (eliminate or reduce) the aberration.

It is possible to perform correction of aberration by hardware or by software. Moreover, it is possible to use a lens of material and shape with small aberration as the head lens 20.

For hardware, it is possible to correct aberration by, for example, regulating the aperture value, introducing an aberration correction optical system in which a concave lens and a convex lens are combined, or use ED glass (low-dispersion optical glass).

For software, image data obtained by intraocular imaging is analyzed. For example, it is possible to correct aberration by adjusting the shape of an observation field to the shape of a cross section (for example, circular) of the illumination light.

The method for correcting aberration is not limited to the abovementioned cross section shape, and it is possible to apply any known method.

Other Modified Example

The observation system 6 may be provided with a diaphragm member (an observation diaphragm). The observation diaphragm effectively acts particularly in observation of the fundus oculi Er of the eye E. The observation diaphragm interrupts unnecessary light such as the reflected light of the illumination light by the cornea or crystalline lens. The aperture value of the observation diaphragm can be set in accordance with a condition such as the pupillary diameter of the eye E, for example. Moreover, as mentioned before, the observation diaphragm can be used as an interrupting part that interrupts a light having entered the observation system 6. The observation diaphragm is placed in any position of the observation system 6, for example, between the magnifying lenses 32a and 32b.

The invention claimed is:

1. A stereomicroscope, comprising:
   an illumination system including a light source configured to output an illumination light and an illumination diaphragm configured to interrupt part of the illumination light, the illumination system being configured to project the illumination light propagated through the illumination diaphragm to an eye;
   an observation system having an objective lens, and right and left optical systems each configured to guide a light reflected by the eye of the illumination light propagated through the objective lens;
   a first mechanism configured to move the illumination system in a lateral direction; and
   a head lens placed between the objective lens and the eye, wherein at the time of intraocular observation of the eye, in a state that an optical axis of the illumination system and an optical axis of the observation system are arranged so as to be nonparallel by the first mechanism and an optical axis of the head lens and an optical axis of the objective lens are arranged so as to be separate in the lateral direction, the illumination light emitted from the illumination system is caused to enter the eye via the head lens, and an intraocularly reflected light of the illumination light is caused to enter the observation system via the head lens.

2. The stereomicroscope according to claim 1, further comprising a second mechanism configured to support the head lens and move the head lens at least in the lateral direction, wherein at the time of intraocular observation of the eye, the optical axis of the head lens and the optical axis of the objective lens are arranged so as to be separate in the lateral direction by the second mechanism.

3. The stereomicroscope according to claim 1, wherein at the time of intraocular observation of the eye, in a state that the illumination system is arranged on one of a right side and a left side of the observation system by the first mechanism and the optical axis of the head lens is arranged on the one side of the optical axis of the objective lens, the intraocularly reflected light is caused to enter the optical system on the one side of the right and left optical systems.

4. The stereomicroscope according to claim 3, wherein the observation system includes an interrupting part configured to interrupt the light having entered the optical system on the other side of the right and left optical systems.

5. The stereomicroscope according to claim 3, wherein the observation system includes a projector configured to project a fixation target to the eye via the optical system on the one side.

6. The stereomicroscope according to claim 1, wherein the first mechanism includes a rotation mechanism configured to support the illumination system so as to be rotatable around an axis orthogonal to the optical axis of the illumination system.

7. The stereomicroscope according to claim 1, wherein the first mechanism includes a first actuator configured to generate a driving force, the first mechanism being configured to move the illumination system by the generated driving force.

8. The stereomicroscope according to claim 7, further comprising:
   a manipulation part; and
   a controller configured to, in response to manipulation of the manipulation part, control the first actuator to move the illumination system so that the optical axis of the illumination system and the optical axis of the observation system form a predetermined angle.

9. The stereomicroscope according to claim 2, wherein the second mechanism is configured to move the head lens in an anteroposterior direction and/or a vertical direction.

10. The stereomicroscope according to claim 9, wherein the second mechanism includes a manipulation part used for moving the head lens.

11. The stereomicroscope according to claim 9, wherein the second mechanism includes a second actuator configured to generate a driving force, the second mechanism being configured to move the head lens by the generated driving force.

12. The stereomicroscope according to claim 11, further comprising:
    a manipulation part; and
    a controller configured to, in response to manipulation of the manipulation part, control the second actuator to move the head lens so that the optical axis of the head lens and the optical axis of the objective lens are separated at a predetermined distance.

13. The stereomicroscope according to claim 2, wherein:
    the illumination system further includes a slitting part configured to form a slit for generating a slit light based on the illumination light outputted from the light source, the illumination system being configured to project the slit light to the eye;
    the first mechanism includes a first actuator configured to generate a driving force, the first mechanism being configured to move the illumination system by the generated driving force; and
    the second mechanism includes a second actuator configured to generate a driving force, the second mechanism being configured to move the head lens by the generated driving force,
    the stereomicroscope further comprising:
    a manipulation part configured to switch from an anterior segment observation mode using the slit light to an intraocular observation mode; and a controller configured to, in response to manipulation of the manipulation part, control the slitting part to end formation of the slit, control the illumination diaphragm to set to a predetermined aperture value, control the first actuator to move the illumination system so that the optical axis of the illumination system and the optical axis of the observation system form a predetermined angle, and control the second actuator to move the head lens so that the optical axis of the head lens and the optical axis of the objective lens are separated at a predetermined distance.

14. The stereomicroscope according to claim 2, wherein:
the illumination system further includes a slitting part configured to generate a slit light based on the illumination light outputted from the light source, the illumination system being configured to project the slit light to the eye;
the first mechanism includes a first actuator configured to generate a driving force, the first mechanism being configured to move the illumination system by the generated driving force; and
the second mechanism includes a second actuator configured to generate a driving force, the second mechanism being configured to move the head lens by the generated driving force,
the stereomicroscope further comprising:
a manipulation part configured to switch from an intraocular observation mode to an anterior segment observation mode using the slit light; and
a controller configured to, in response to manipulation of the manipulation part, control the illumination diaphragm to set to an open aperture value, and control the slitting part to form the slit.

15. The stereomicroscope according to claim 1, further comprising:
a storage configured to previously store angle relation information that relates a power of the head lens and an angle of the optical axis of the illumination system with respect to the optical axis of the observation system; and
a controller configured to receive power information of the head lens placed between the objective lens and the eye, obtain an angle corresponding to the power represented in the power information with reference to the angle relation information, and control the first mechanism based on the obtained angle to move the illumination system.

16. The stereomicroscope according to claim 2, wherein the second mechanism is configured to also move the head lens in an anteroposterior direction,
the stereomicroscope further comprising:
a storage configured to previously store distance relation information that relates a power of the head lens and a distance between the head lens and the objective lens; and
a controller configured to receive power information of the head lens placed between the objective lens and the eye, obtain a distance corresponding to the power represented in the power information with reference to the distance relation information, and control the second mechanism based on the obtained distance to move the head lens in the anteroposterior direction.

17. The stereomicroscope according to claim 2, further comprising:
a storage configured to previously store displacement relation information that relates a power of the head lens and a displacement in the lateral direction of the optical axis of the head lens with respect to the optical axis of the objective lens; and
a controller configured to receive power information of the head lens placed between the objective lens and the eye, obtain a displacement corresponding to the power represented in the power information with reference to the displacement relation information, and control the second mechanism based on the obtained displacement to move the head lens in the lateral direction.

18. The stereomicroscope according to claim 2, wherein the second mechanism includes a mount to which a plurality of head lenses having different powers are selectively mounted, and an indicator configured to indicate a position to mount each of the plurality of head lenses to the mount.

19. The stereomicroscope according to claim 1, wherein the first mechanism includes an indicator configured to indicate a position of the illumination system corresponding to each of a plurality of head lenses having different powers.

20. The stereomicroscope according to claim 1, further comprising a corrector configured to correct aberration caused in a state that the optical axis of the illumination system and the optical axis of the observation system are arranged so as to be nonparallel and the optical axis of the head lens and the optical axis of the objective lens are arranged so as to be separate in the lateral direction.

* * * * *